(12) United States Patent
Arrhenius et al.

(10) Patent No.: US 7,385,063 B2
(45) Date of Patent: Jun. 10, 2008

(54) METHOD FOR PREPARING IMIDAZOLE DERIVATIVES

(75) Inventors: Thomas Arrhenius, Del Mar, CA (US); Mi Chen, San Diego, CA (US); Jie Fei Cheng, Carlsbad, CA (US); Yujin Huang, San Diego, CA (US); Alex Michael Nadzan, Encinitas, CA (US); Sovouthy Tith, San Diego, CA (US); Masayuki Haramura, Chiba (JP); David Mark Wallace, San Diego, CA (US); Steve Joel Brown, San Diego, CA (US); Charles Stanford Harmon, Rancho Santa Fe, CA (US); Lin Zhang, San Diego, CA (US); Gary D. Lopaschuk, Edmonton (CA); Jason R. Dyck, Sherwood Park (CA)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 522 days.

(21) Appl. No.: 10/466,856

(22) PCT Filed: Jan. 22, 2002

(86) PCT No.: PCT/US02/01814

§ 371 (c)(1),
(2), (4) Date: Jul. 21, 2003

(87) PCT Pub. No.: WO02/058690

PCT Pub. Date: Aug. 1, 2002

(65) Prior Publication Data

US 2004/0087627 A1   May 6, 2004

Related U.S. Application Data

(60) Provisional application No. 60/265,380, filed on Jan. 26, 2001, provisional application No. 60/264,552, filed on Jan. 26, 2001.

(51) Int. Cl.
  *C07D 233/00* (2006.01)
  *C07D 233/02* (2006.01)
  *A01N 43/50* (2006.01)
  *A61K 31/415* (2006.01)

(52) U.S. Cl. .................... 548/300.1; 514/396
(58) Field of Classification Search ............. 514/396; 548/300.1
  See application file for complete search history.

(56) References Cited

U.S. PATENT DOCUMENTS

| 5,177,097 | A | 1/1993 | Poss |
|---|---|---|---|
| 5,190,942 | A | 3/1993 | Poss |
| 5,208,234 | A | 5/1993 | Poss |
| 5,208,235 | A | 5/1993 | Poss |
| 5,212,177 | A | 5/1993 | Poss |
| 5,225,408 | A | 7/1993 | Weller |
| 5,256,695 | A | 10/1993 | Poss |
| 5,374,615 | A | 12/1994 | Poss |
| 5,378,704 | A | 1/1995 | Weller |
| 5,428,033 | A | 6/1995 | Belley |
| 5,470,975 | A | 11/1995 | Atwal |
| 5,512,681 | A | 4/1996 | Boswell |
| 5,519,143 | A | 5/1996 | Harris |
| 5,534,347 | A | 7/1996 | Chen |
| 5,736,297 | A | 4/1998 | Roeschert |
| 5,895,771 | A | 4/1999 | Epstein |
| 5,977,413 | A | 11/1999 | Tomaru |
| 2004/0082576 | A1* | 4/2004 | Arrhenius et al. ....... 514/227.5 |

FOREIGN PATENT DOCUMENTS

| DE | 197 16 231 A1 | 10/1998 |
|---|---|---|
| DE | 197 22 952 A1 | 12/1998 |
| EP | 0 296 722 A1 | 12/1988 |
| EP | 0 481 448 A1 | 4/1992 |
| EP | 0 547 442 A1 | 6/1993 |
| EP | 0 556 060 A1 | 8/1993 |
| EP | 0733 366 A2 | 9/1996 |
| EP | 0 733 614 A1 | 5/1998 |
| EP | 0 916 352 A2 | 12/1998 |

(Continued)

OTHER PUBLICATIONS

Trisha Gura, Systems for Identifying New Drugs are Often Faulty, 1997, Science, vol. 278, No. 7, pp. 1041-1042.*

(Continued)

*Primary Examiner*—Sreeni Padmanabhan
*Assistant Examiner*—Kendra D. Carter
(74) *Attorney, Agent, or Firm*—Fish & Richardson P.C.

(57) ABSTRACT

The present invention relates to methods for the prophylaxis, management and treatment of certain diseases modulated by the inhibition of the enzyme malonyl-coenzyme A decarboxylase (malonyl-CoA decarboxylase, MCD) by the administration of a composition containing as an active ingredient a compound according to Formula I. In particular, the invention relates to methods for the prophylaxis, management and treatment of cardiovascular diseases, diabetes, acidosis, cancers, and obesity through the administration of a compound which inhibits malonyl-coenzyme A decarboxylase activity. The present invention also includes within its scope the novel process for the preparation of certain compounds

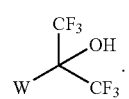

(I)

12 Claims, No Drawings

FOREIGN PATENT DOCUMENTS

| | | |
|---|---|---|
| FR | 2 784 114 A1 | 4/2000 |
| GB | 2 321 244 A | 7/1998 |
| GB | 2 337 701 A | 1/1999 |
| JP | 08 311036 | 11/1996 |
| JP | 09 012585 | 1/1997 |
| JP | 2007-185377 | 7/2007 |
| RU | 1825496 A3 | 12/1994 |
| RU | 1743153 | 2/1995 |
| WO | WO 87/05297 | 9/1987 |
| WO | WO 91/00277 | 1/1991 |
| WO | WO 91/00281 | 1/1991 |
| WO | WO 92/00067 | 1/1992 |
| WO | WO 93/21158 | 10/1993 |
| WO | WO 93/21168 | 10/1993 |
| WO | WO 94/10692 | 5/1994 |
| WO | WO 94/14453 | 7/1994 |
| WO | WO 94/15932 | 7/1994 |
| WO | WO 94/18606 | 8/1994 |
| WO | WO 95/35311 | 12/1995 |
| WO | WO 95/35313 | 12/1995 |
| WO | WO 96/13491 | 5/1996 |
| WO | WO 96/13500 | 5/1996 |
| WO | WO 99/12938 | 3/1999 |
| WO | WO 99/47497 | 9/1999 |
| WO | WO 95/35312 | 12/1999 |
| WO | WO 00/20472 | 4/2000 |
| WO | WO 00/34344 | 6/2000 |
| WO | WO 00/37422 | 6/2000 |
| WO | WO 00/46203 | 8/2000 |
| WO | WO 00/54759 | 9/2000 |
| WO | WO 00/56710 | 9/2000 |
| WO | WO 0054759 A2 * | 9/2000 |
| WO | WO 01/03705 | 1/2001 |

OTHER PUBLICATIONS

Abo-Hashema, et al., Biochemistry, 1999, 15840-15847, vol 38.
Abo-Hashema, et al., Journal of Biological Chemistry, 1999, 35577-35582, Vo. 274, No. 50.
Alam and Saggerson, Biochen J., 1998, 233-241, vol. 334.
An, et al., Journal of Biochemistry and Molecular Biology, 1999, 414-418, vol. 32, No. 4.
Anderson, Current Pharmaceutical Design, 1998, 1-16, vol. 4, No. 1.
Buckner, et al., Archives of Biochemistry and Biophysics, 1976, 539-551, vol. 177.
Deems, et al., The American Physiological Society, 1998, R524-R528, vol. 274.
Dyck, et al., The American Physiological Society, 1998, H2122-H2129, vol. 275.
Fitzpatrick, et. al., Am. J. Hum. Genet. 1999, 318-326, vol. 65.
Fraser, et al., Febs Letters, 1999, 69-74, vol. 446.
Gao, et al., Journal of Lipid Research, 1999, 178-182, vol. 40.
Hearse, Metabolic Approaches to Ischaemic Heart Disease and its Management, Science Press, London, UK.
Jang, et al., The Journal of Biological Chemistry, 1989, 3500-3505, vol. 264, No. 6.
Kantor, et al., Circulation Research, 2000, 580-588, vol. 86.
Kennedy, et. al., Biochemical Pharmacology, 1996, 273-280, vol. 52.
Kim and Kolattukudy, Archives of Biochemistry and Biophysics, 1978, 585-597, vol. 190, No. 2.
Kim and Kolattukudy, Archives of Biochemistry and Biophysics, 1978, 234-246, vol. 190, No. 1.
Kim and Kolattukudy, Biochimica et Biophysica Acta, 1978, 187-196, vol. 531.
Loftus, et al., Science, 2000, 237-238, vol. 288.
McCormack, et al., Gen. Pharmac., 1998, 639-645, vol. 30, No. 5.
McGarry and Brown, Eur. J. Biochem, 1997, 1-14, vol. 244.
Pepine and Wolff, The American Journal of Cardiology, 1999, 46-50, vol. 84.
Pizer, et al., Cancer Research, 2000, 213-218, vol. 60.
Prentki and Corkey, Diabetes, 1996, 273-283, vol. 45.
Randle, et al., Lancet, 1963, 785-789, vol. 1.
Sacksteder, et al., The Journal of Biological Chemistry, 1999, 24461-24468, vol. 274, No. 35.
Voilley, et al., Biochem J., 1999, 213-217, vol. 340.
Wargovich, et. al., Am J Cardiol, 1998, 65-70, vol. 61.
Zammit, Biochemical Society, 1999, 505-515, vol. 343.

* cited by examiner

METHOD FOR PREPARING IMIDAZOLE DERIVATIVES

This application claims the benefits of provisional applications Ser. Nos. 60/265,380 and 60/264,552 filed on Jan. 26, 2001. The entire disclosure is incorporated herein by reference.

FIELD OF THE INVENTION

The present invention relates to methods for the prophylaxis, management and treatment of certain diseases modulated by the inhibition of the enzyme malonyl-coenzyme A decarboxylase (malonyl-CoA decarboxylase, MCD) by the administration of a composition containing as an active ingredient a compound according to Formula I. In particular, the invention relates to methods for the prophylaxis, management and treatment of cardiovascular diseases, diabetes, acidosis, cancers, and obesity through the administration of a compound which inhibits malonyl-coenzyme A decarboxylase activity. The present invention also includes within its scope the novel process for the preparation of certain compounds.

BACKGROUND

Malonyl-CoA is an important metabolic intermediary produced by the enzyme Acetyl CoA Carboxylase (ACC) in the body. In the liver, adipocytes, and other tissues, malonyl-CoA is a substrate for fatty acid synthase (FAS). ACC and malonyl-CoA are found in skeletal muscle and cardiac muscle tissue, where fatty acid synthase levels are low. The enzyme malonyl-CoA decarboxylase (MCD, EC 4.1.1.9) catalyzes the conversion of malonyl-CoA to acetyl-CoA and thereby regulates malonyl-CoA levels. MCD activity has been described in a wide array of organisms, including prokaryotes, birds, and mammals. It has been purified from the bacteria *Rhizobium trifolii* (An et al., *J. Biochem. Mol. Biol.* 32:414-418(1999)), the uropygial glands of waterfowl (Buckner, et al., *Arch. Biochem. Biophys* 177:539(1976); Kim and Kolattukudy *Arch. Biochem. Biophys* 190:585 (1978)), rat liver mitochondria (Kim and Kolattukudy, *Arch. Biochem. Biophys*. 190:234(1978)), rat mammary glands (Kim and Kolattukudy, *Biochim. Biophys, Acta* 531:187 (1978)), rat pancreatic β-cell (Voilley et al., *Biochem. J.* 340:213 (1999)) and goose (Anser anser) (Jang et al., *J. Biol. Chem.* 264:3500 (1989)). Identification of patients with MCD deficiency led to the cloning of a human gene homologous to goose and rat MCD genes (Gao et al., *J. Lipid. Res.* 40:178 (1999); Sacksteder et al., *J. Biol. Chem.* 274:24461 (1999); FitzPatrick et al., *Am. J. Hum. Genet.* 65:318(1999)). A single human MCD mRNA is observed by Northern Blot analysis. The highest mRNA expression levels are found in muscle and heart tissues, followed by liver, kidney and pancreas, with detectable amounts in all other tissues examined.

Malonyl-CoA is a potent endogenous inhibitor of carnitine palmitoyltransferase-I (CPT-I), an enzyme essential for the metabolism of long-chain fatty acids. CPT-I is the rate-limiting enzyme in fatty acid oxidation and catalyzes the formation of acyl-carnitine, which is transported from the cytosol across the mitochondrial membranes by acyl carnitine translocase. Inside of the mitochondria the long-chain fatty acids are transferred back to CoA form by a complementary enzyme, CPT-II, and, in the mitochondria, acyl-CoA enters the β-oxidation pathway generating acetyl-CoA. In the liver, high levels of acetyl-CoA occur for example following a meal, leading to elevated malonyl-CoA levels, which inhibit CPT-I, thereby preventing fat metabolism and favoring fat synthesis. Conversely, low malonyl-CoA levels favor fatty acid metabolism by allowing the transport of long-chain fatty acids into the mitochondria. Hence, malonyl-CoA is a central metabolite that plays a key role in balancing fatty acid synthesis and fatty acid oxidation (Zammit, *Biochem. J.* 343:5050-515(1999)). Recent work indicates that MCD is able to regulate cytoplasmic as well as mitochondrial malonyl-CoA levels [Alam and Saggerson, *Biochem J.* 334:233-241(1998); Dyck et al., *Am J Physiology* 275:H2122-2129(1998)].

Although malonyl-CoA is present in muscle and cardiac tissues, only low levels of FAS have been detected in these tissues. It is believed that the role of malonyl-CoA and MCD in these tissues is to regulate fatty acid metabolism. This is achieved via malonyl-CoA inhibition of muscle (M) and liver (L) isoforms of CPT-I, which are encoded by distinct genes (McGarry and Brown, *Eur. J. Biochem.* 244:1-14 (1997)). The muscle isoform is more sensitive to malonyl-CoA inhibition (IC50 0.03 μM) than the liver isoform ($IC_{50}$ 2.5 μM). Malonyl-CoA regulation of CPT-I has been described in the liver, heart, skeletal muscle and pancreatic β-cells. In addition, malonyl-CoA sensitive acyl-CoA transferase activity present in microsomes, perhaps part of a system that delivers acyl groups into the endoplasmic reticulum, has also been described (Fraser et al., *FEBS Lett*. 446: 69-74 (1999)).

Cardiovascular Diseases: The healthy human heart utilizes available metabolic substrates. When blood glucose levels are high, uptake and metabolism of glucose provide the major source of fuel for the heart. In the fasting state, lipids are provided by adipose tissues, and fatty acid uptake and metabolism in the heart down regulate glucose metabolism. The regulation of intermediary metabolism by serum levels of fatty acid and glucose comprises the glucose-fatty acid cycle (Randle et al., *Lancet*, 1:785-789(1963)). Under ischemic conditions, limited oxygen supply reduces both fatty acid and glucose oxidation and reduces the amount of ATP produced by oxidative phosphorylation in the cardiac tissues. In the absence of sufficient oxygen, glycolysis increases in an attempt to maintain ATP levels and a buildup of lactate and a drop in intracellular pH results. Energy is spent maintaining ion homeostasis, and myocyte cell death occurs as a result of tissue acidification, abnormally low ATP levels and disrupted cellular osmolarity. Additionally, AMPK, activated during ischemia, phosphorylates and thus inactivates ACC. Total cardiac malonyl-CoA levels drop, CPT-I activity therefore is increased and fatty acid oxidation is favored over glucose oxidation. The beneficial effects of metabolic modulators in cardiac tissue are the increased efficiency of ATP/mole oxygen for glucose as compared to fatty acids and more importantly the increased coupling of glycolysis to glucose oxidation resulting in the net reduction of the proton burden in the ischemic tissue.

A number of clinical and experimental studies indicate that shifting energy metabolism in the heart towards glucose oxidation is an effective approach to decreasing the symptoms associated with cardiovascular diseases, such as but not limited, to myocardial ischemia (Hearse, "*Metabolic approaches to ischemic heart disease and its management*", Science Press). Several clinically proven anti-angina drugs including perhexiline and amiodarone inhibit fatty acid oxidation via inhibition of CPT-I (Kennedy et al., *Biochem. Pharmacology*, 52: 273 (1996)). The antianginal drugs ranolazine and trimetazidine are shown to inhibit fatty acid β-oxidation (McCormack et al., *Genet. Pharmac*. 30:639

(1998), Pepine et al., *Am. J. Cardiology* 84:46 (1999)). Trimetazidine has been shown to specifically inhibit the long-chain 3-ketoactyl CoA thiolase, an essential step in fatty acid oxidation. (Kantor et al., *Circ. Res.* 86:580-588 (2000)). Dichloroacetate increases glucose oxidation by stimulating the pyruvate dehydrogenase complex and improves cardiac function in those patients with coronary artery diseases (Wargovich et al., *Am. J. Cardiol.* 61:65-70 (1996)). Inhibiting CPT-I activity through the increased malonyl-CoA levels with MCD inhibitors would result in not only a novel, but also a much safer method, as compared to other known small molecule CPT-I inhibitors, to the prophylaxis and treatment of cardiovascular diseases.

Most of the steps involved in glycerol-lipid synthesis occur on the cytosolic side of liver endoplasmic reticulum (ER) membrane. The synthesis of triacyl glycerol (TAG) targeted for secretion inside the ER from diacyl gycerol (DAG) and acyl CoA is dependent upon acyl CoA transport across the ER membrane. This transport is dependent upon a malonyl-CoA sensitive acyl-CoA transferase activity (Zammit, *Biochem. J.* 343: 505(1999) Abo-Hashema, *Biochem.* 38: 15840 (1999) and Abo-Hashema, *J. Biol Chem.* 274:35577 (1999)). Inhibition of TAG biosynthesis by a MCD inhibitor may improve the blood lipid profile and therefore reduce the risk factor for coronary artery disease of patients.

Diabetes: Two metabolic complications most commonly associated with diabetes are hepatic overproduction of ketone bodies (in NIDDM) and organ toxicity associated with sustained elevated levels of glucose. Inhibition of fatty acid oxidation can regulate blood-glucose levels and ameliorate some symptoms of type II diabetes. Malonyl-CoA inhibition of CPT-I is the most important regulatory mechanism that controls the rate of fatty acid oxidation during the onset of the hypoinsulinemic-hyperglucagonemic state. Several irreversible and reversible CPT-I inhibitors have been evaluated for their ability to control blood glucose levels and they are all invariably hypoglycemic (Anderson, *Current Pharmaceutical Design* 4:1(1998)). A liver specific and reversible CPT-inhibitor, SDZ-CPI-975, significantly lowers glucose levels in normal 18-hour-fasted nonhuman primates and rats without inducing cardiac hypertrophy (Deems et al., *Am. J. Physiology* 274:R524 (1998)). Malonyl-CoA plays a significant role as a sensor of the relative availability of glucose and fatty acid in pancreatic β-cells, and thus links glucose metabolism to cellular energy status and insulin secretion. It has been shown that insulin secretagogues elevate malonyl-CoA concentration in β-cells (Prentki et al., *Diabetes* 45: 273 (1996)). Treating diabetes directly with CPT-I inhibitors has, however, resulted in mechanism-based hepatic and myocardial toxicities. MCD inhibitors that inhibit CPT-I through the increase of its endogenous inhibitor, malonyl-CoA, are thus safer and superior as compared to CPT-I inhibitors for treatment of diabetic diseases.

Cancers: Malonyl-CoA has been suggested to be a potential mediator of cytotoxicity induced by fatty-acid synthase inhibition in human breast cancer cells and xenografts (Pizer et al., *Cancer Res.* 60:213 (2000)). It is found that inhibition of fatty acid synthase using antitumor antibiotic cerulenin or a synthetic analog C75 markedly increase the malonyl-CoA levels in breast carcinoma cells. On the other hand, the fatty acid synthesis inhibitor, TOFA (5-(tetradecyloxy)-2-furoic acid), which only inhibits at the acetyl-CoA carboxylase (ACC) level, does not show any antitumor activity, while at the same time the malonyl-CoA level is decreased to 60% of the control. It is believed that the increased malonyl-CoA level is responsible for the antitumor activity of these fatty acid synthase inhibitors. Regulating malonyl-CoA levels using MCD inhibitors thus constitutes a valuable therapeutic strategy for the treatment of cancer diseases.

Obesity: It is suggested that malonyl-CoA may play a key role in appetite signaling in the brain via the inhibition of the neuropepetide Y pathway (Loftus et al., *Science* 288: 2379 (2000)). Systemic or intracerebroventricular treatment of mice with fatty acid synthase (FAS) inhibitor cerulenin or C75 led to inhibition of feeding and dramatic weight loss. It is found that C75 inhibited expression of the prophagic signal neuropeptide Y in the hypothalamus and acted in a leptin-independent manner that appears to be mediated by malonyl-CoA. Therefore control of malonyl-CoA levels through inhibition of MCD provides a novel approach to the prophylaxis and treatment of obesity.

SUMMARY OF THE INVENTION

The present invention provides novel methods for the prophylaxis, management and treatment of metabolic diseases and diseases modulated by MCD inhibition by the administration of a compound according to Formula (I). In particular, these methods and pharmaceutical composition containing such compounds are indicated in the prophylaxis, management and treatment of cardiovascular diseases, diabetes, acidosis, cancers and obesity.

According to the present invention, the method comprises the administration of a compound as depicted by Formula (I):

(I)

in a pharmaceutically acceptable carrier, wherein W is as defined below.

According to another embodiment of the present invention, certain compounds are prepared by a novel process, which is more fully described below.

DETAILED DESCRIPTION OF THE INVENTION

The detailed description of the invention that follows is not intended to be exhaustive or to limit the invention to the precise details disclosed. It has been chosen and described to best explain the details of the invention to others skilled in the art.

The method of the invention relates to the administration of a compound as depicted by Formula (I):

(I)

wherein W is independently selected from:
a five or six membered aromatic ring or aromatic heterocyclic ring with respective substituents represented by the following structures:

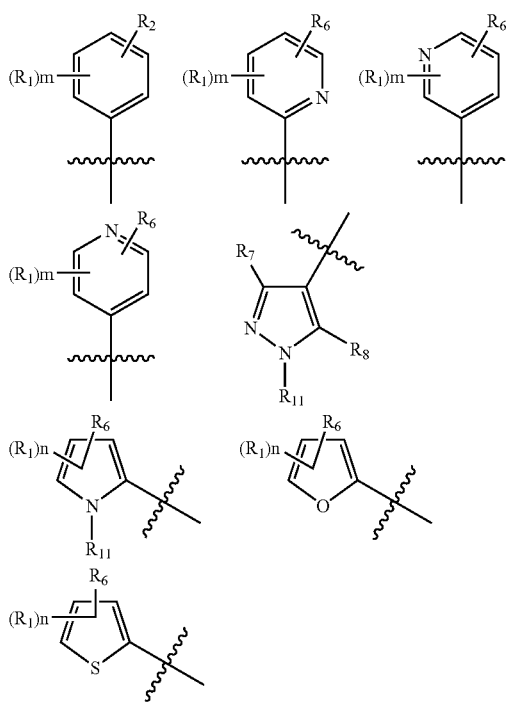

wherein

R$_1$ is independently chosen from halo, haloalkyl, hydroxy, thiol, substituted thiol, sulfonyl, sulfinyl, nitro, cyano, amino, substituted amino, C$_1$-C$_6$ alkyl and C$_1$-C$_6$ alkoxy, and when R$_1$ is hydroxy, C$_1$-C$_6$ alkoxy, thiol, substituted thiol, amino, substituted amino, or C$_1$-C$_6$ alkyl, such radical may be combined with R$_2$ or R$_6$ to form a ring of 5-7 members when R$_1$ is ortho to R$_2$ or R$_6$;

R$_2$ is selected from alkyl, OR$_3$, NR$_4$R$_5$, SR$_3$, NR$_3$C(O)NR$_4$R$_5$, NR$_3$COR$_4$, NR$_3$CSR$_4$, CONR$_4$R$_5$, NR$_3$SO$_2$R$_4$, NR$_3$SO$_2$NR$_4$R$_5$, a five membered ring with the following structures:

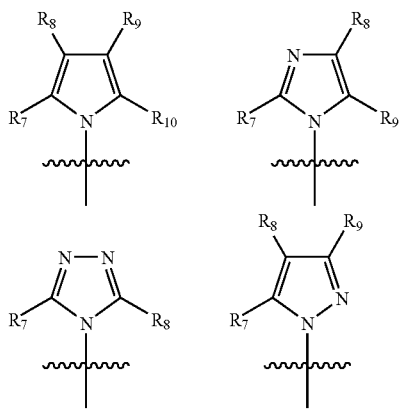

or may be combined with R$_1$ to form a ring of 5-7 members when R$_2$ is ortho to R$_1$;

R$_3$ is hydrogen, alkyl, aryl, heterocyclyl, or may form a ring of 5-7 members with R$_4$ or R$_5$;

R$_4$ is hydrogen, alkyl, aryl, heterocyclyl, or may form a ring of 5-7 members with R$_5$ or R$_3$;

R$_5$ is hydrogen, alkyl, aryl, or heterocyclyl, or may form a ring of 5-7 members with R$_3$ or R$_4$;

R$_6$ is selected from alkyl, OR$_3$, NR$_4$R$_5$, SR$_3$, NR$_3$C(O)NR$_4$R$_5$, NR$_3$COR$_4$, NR$_3$CSR$_4$, CONR$_4$R$_5$, NR$_3$SO$_2$R4, NR$_3$SO$_2$NR$_4$R$_5$, or may be combined with R$_1$ to form a ring of 5-7 members when R$_6$ is ortho to R$_1$;

R$_7$, R$_8$, R$_9$, and R$_{10}$ may be equal or different and are selected from hydrogen, alkyl, aryl, heterocyclyl, nitro, cyano, carboxylic acid, ester, amide, halo, hydroxyl, amino, substituted amino, alkoxy, acyl, ureido, sulfonamido, sulfamido, sulfonyl, sulfinyl, or guanadinyl;

R$_{11}$ is hydrogen, alkyl, aryl, heterocyclyl, acyl, ester, sulfonyl, ureido, or guanadinyl;

m is from zero to four;

n is from zero to two;

Z is O, S or NR$_{11}$;

its corresponding enantiomers, diastereoisomers or tautomers;

or a pharmaceutically acceptable salt, or a prodrug thereof in a pharmaceutically-acceptable carrier.

Preferably, the method of this invention comprises the administration of a compound as depicted by the following general structures in a pharmaceutically-acceptable carrier:

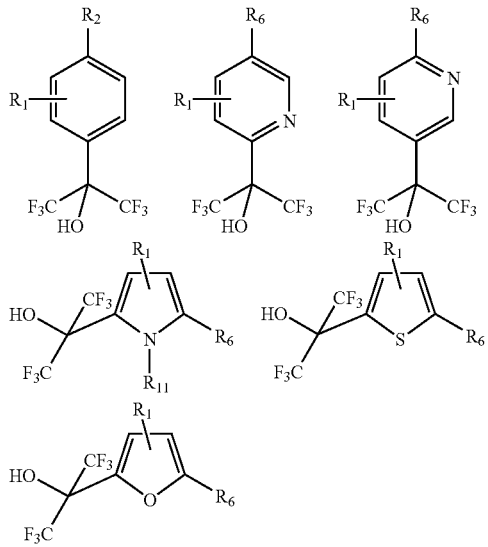

wherein R$_1$, R$_2$, R$_6$ and R$_{11}$ are as defined above.

More preferably, the method of this invention comprises the administration of a compound as depicted by the following general structures in a pharmaceutically-acceptable carrier:

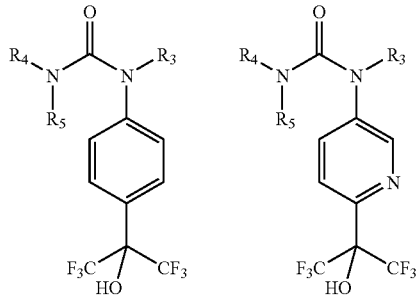

-continued

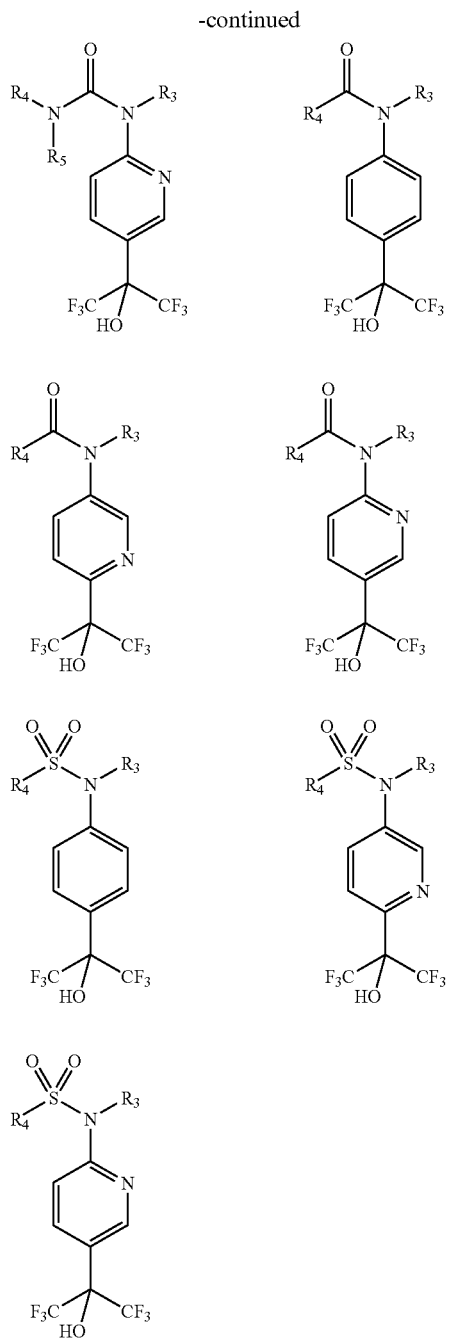

wherein $R_3$, $R_4$, and $R_5$ are is as defined above and Z is $NR_{11}$, O or S.

Still more preferably, the method of this invention comprises the pound as depicted by the following general structures in a pharmaceutically-acceptable carrier:

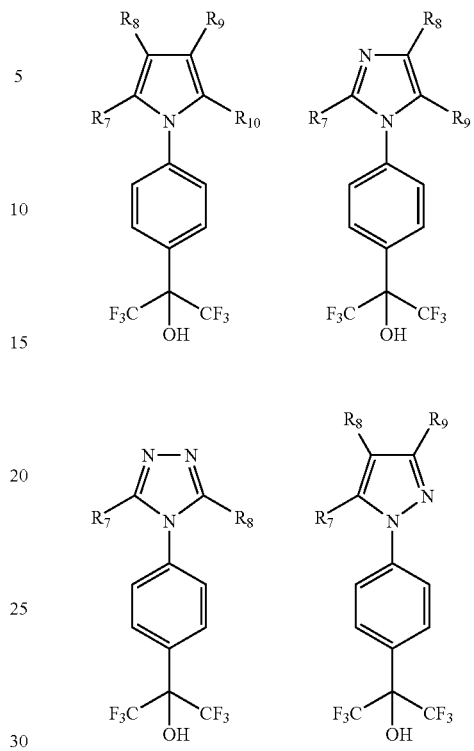

wherein $R_7$, $R_8$, $R_9$ and $R_{10}$ are as defined above.

In accordance with the novel process of this invention, the above described substituted imidazole derivatives are prepared according to Scheme 3.

Thus, as shown in Scheme 3, imidazole derivatives are prepared from an amidine intermediate XI which in turn is prepared from the aniline derivatives and nitriles in the presence of a Lewis acid at elevated temperature or in the presence of a strong base such as lithium hexamethyldisilyl amide. In the next step, the amidine is treated with an activated α-haloketone or α-haloaldehyde yielding the desired imidazole ring system. The resulting imidazole compounds, for example, XIIIa and XIIIb, are further modified to give other derivatives such as compounds XIV.

Definitions

As used herein, "alkyl" means a cyclic, branched, or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C=C— or —C≡C— subunits), at one or several positions. Typically, alkyl groups will comprise 1 to 12 carbon atoms, preferably 1 to 10, and more preferably 1 to 8 carbon atoms or cyclic groups containing three to eight carbons.

As used herein, "lower alkyl" means a subset of alkyl, and thus is a hydrocarbon substituent, which is linear, cyclic or branched. Preferred lower alkyls are of 1 to about 6 carbons, and may be branched or linear, and may include cyclic substituents, either as part or all of their structure. Examples of lower alkyl include butyl, propyl, isopropyl, ethyl, and methyl. Likewise, radicals using the terminology "lower" refer to radicals preferably with 1 to about 6 carbons in the alkyl portion of the radical.

As used herein, "amido" means a H—CON— or alkyl-CON—, aryl-CON— or heterocyclyl-CON group wherein the alkyl, aryl or heterocyclyl group is as herein described.

As used herein, "aryl" means a substituted or unsubstituted aromatic radical having a single-ring (e.g., phenyl) or multiple condensed rings (e.g., naphthyl or anthryl), which can be optionally unsubstituted or substituted with amino, cyano, hydroxyl, lower alkyl, haloalkyl, alkoxy, nitro, halo, mercapto, and other substituents, and which may or may not include one or more heteroatoms. Preferred carbocyclic aryl is phenyl. The term "heteroaryl" is clearly contemplated in the term "aryl". Preferably where the term aryl represents a heterocycle, it is referred to as "heteroaryl", and has one or more heteroatom(s). Preferred are monocyclic heterocycles of 5 or 6 members. Hence preferred heteroaryl is a monovalent unsaturated aromatic group having a single ring and having at least one hetero atom, such as N, O, or S, within the ring, which can optionally be unsubstituted or substituted with amino, cyano, nitro, hydroxyl, alkyl, haloalkyl, alkoxy, aryl, halo, mercapto, oxo (hence forming a carbonyl.) and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In this definition it is clearly contemplated that substitution on the aryl ring is within the scope of this invention. Where substitution occurs, the radical is called substituted aryl. Preferably one to three, more preferably one or two, and most preferably one substituent occur on the aryl ring. Preferred substitution patterns in five membered rings are substituted in the 2 position relative to the connection to the claimed molecule. Though many substituents will be useful, preferred substituents include those commonly found in aryl compounds, such as alkyl, hydroxy, alkoxy, cyano, nitro, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, aryl-CO— or heterocyclyl-CO— group wherein the alkyl, aryl or heterocyclcyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 5 carbons in length, More preferred haloalkyls are 1 to about 4 carbons, and most preferred are 1 to 3 carbons in length. The skilled artisan will recognize then that as used herein, "haloalkylene" means a diradical variant of haloalkyl, such diradicals may act as spacers between radicals, other atoms, or between the parent ring and another functional group. For example, the linker CHF—CHF is a haloakylene diradical.

As used herein, "heterocyclyl" means heterocyclic radicals, which are saturated or unsaturated. These may be substituted or unsubstituted, and are attached to other via any available valence, preferably any available carbon or nitrogen. More preferred heterocycles are of 5 or 6 members. In six membered non-aromatic monocyclic heterocycles, the heteroatom(s) are selected from one up to three of O, N or S, and wherein when the heterocycle is five membered and non-aromatic, preferably it has one or two heteroatoms selected from O, N, or S.

As used herein, "substituted amino" means an amino radical which is substituted by one or two alkyl, aryl, or heterocyclyl groups, wherein the alkyl, aryl or heterocyclyl are defined as above.

As used herein, "substituted thiol" means RS— group wherein R is an alkyl, an aryl, or a heterocyclyl group, wherein the alkyl, aryl or heterocyclyl are defined as above.

As used herein, "sulfonyl" means an alkylSO$_2$, arylSO$_2$ or heterocyclyl-SO$_2$ group wherein the alkyl, aryl or heterocyclyl are defined as above.

As used herein, "sulfamido" means an alkyl-N—S(O)$_2$N—, aryl-NS(O)$_2$N— or heterocyclyl-NS(O)$_2$N— group wherein the alkyl, aryl or heterocyclyl group is as herein described.

As used herein, "sulfonamido" means an alkyl-S(O)$_2$N—, aryl-S(O)$_2$N— or heterocyclyl-S(O)$_2$N— group wherein the alkyl, aryl or heterocyclcyl group is as herein described.

As used herein, "ureido" means an alkyl-NCON—, aryl-NCON— or heterocyclyl-NCON— group wherein the alkyl, aryl or heterocyclcyl group is as herein described As used herein, a "radical" in this specification may form a ring with another radical as described herein. When such radicals are combined, the skilled artisan will understand that there are no unsatisfied valences in such a case, but that specific substitutions, for example a bond for a hydrogen, is made. Hence certain radicals can be described as forming rings together. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic or carbocyclic radicals, and such radicals may be saturated, unsaturated, or aromatic. For example, preferred heterocyclic ring systems include heterocyclic rings, such as morpholinyl, piperdinyl, imidazolyl, pyrrolidinyl, and pyridyl.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein. For example,

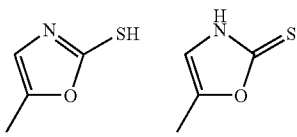

the above substructures clearly represent the same radical and reference to either clearly contemplates the other. In addition, the following compounds may represent prodrugs when R can be removed by biological processes in situ:

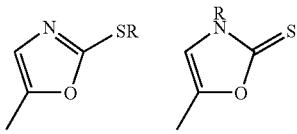

Compounds and compositions herein also, specifically contemplate pharmaceutically acceptable salts, whether cationic or anionic. A "pharmaceutically-acceptable salt" is an anionic salt formed at any acidic (e.g., carboxyl) group, or a cationic salt formed at any basic (e.g., amino) group. Many such salts are known in the art, as described in World Patent Publication 87/05297, Johnston et al., published Sep. 11, 1987 (incorporated by reference herein). Preferred counterions of salts formable at acidic groups can include cations of salts, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of either organic or inorganic salts useful in this manner.

It is also clearly contemplated that compounds useful for the methods of this invention can be provided as biohydrolyzable prodrugs, as they are understood in the art. "Prodrug", as used herein is any compound wherein when it is exposed to the biological processes in an organism, is hydrolyzed, metabolized, derivatized or the like, to yield an active substance having the desired activity. The skilled artisan will recognize that prodrugs may or may not have any activity as prodrugs. It is the intent that the prodrugs described herein have no deleterious effect on the subject to be treated when dosed in safe and effective amounts. These include for example, biohydrolyzable amides and esters. A "biohydrolyzable amide" is an amide compound which does not essentially interfere with the activity of the compound, or that is readily converted in vivo by a cell, tissue, or human, mammal, or animal subject to yield an active compound of the invention. A "biohydrolyzable ester" refers to an ester compound of the invention that does not interfere with the activity of these compounds or that is readily converted by an animal to yield an active formula (I) compound. Such biohydrolyzable prodrugs are understood by the skilled artisan and are embodied in regulatory guidelines.

Inasmuch as the compounds useful for this invention may contain optical centers, "optical isomer", "stereoisomer", "enantiomer," "diastereomer," as referred to herein have the standard art recognized meanings (cf. *Hawleys Condensed Chemical Dictionary*, 11th Ed.) and are included in the compounds claimed, whether as racemates, or their optical isomers, stereoisomers, enantiomers, diastereomers.

As used herein "cardiovascular diseases" include arrhthymia, atrial fibrillation, congestive heart failure, coronary artery disease, hypertension, myocardial infarction, stroke, ventricular fibrillation, among others, particularly cardiovascular ischemia such as angina pectoris and those conditions treatable by shifting metabolism within the cardiovascular system.

As used herein, "metabolic disease" means disorders in a mammal in which errors of metabolism, imbalances in metabolism, or sub-optimal metabolism occur. The metabolic diseases as used herein also contemplate a disease that can be treated through the modulation of metabolism, although the disease itself may or may not be caused by specific metabolism blockage. Particularly, such metabolic disease involves glucose and fatty acid oxidation pathway. Still more particularly, such metabolic disease involves MCD or is modulated by levels of Malonyl-CoA. All these conditions are collectively referred to herein as an "MCD or MCA related disorder."

Compositions

The Compositions of the Present Invention Comprise:
(a) a safe and therapeutically effective amount of an MCD inhibiting compound (I), prodrug or pharmaceutical salt thereof; and
(b) a pharmaceutically-acceptable carrier.

As discussed above, numerous diseases can be mediated by MCD related therapy. Thus, the methods of this invention are useful in therapy with regard to conditions involving this MCD activity.

Accordingly, to treat such diseases the selected compound is formulated into pharmaceutical compositions for use in prophylaxis, management and treatment of these conditions. Standard pharmaceutical formulation techniques such as tablets, capsules and like are used. These dosage forms are prepared by known techniques, for example, those disclosed in Remington's Pharmaceutical Sciences, Mack Publishing Company, Easton, Pa.

A "safe and therapeutically effective amount" of a compound used in the present methods is an amount that is effective, to inhibit MCD at the site(s) of activity, in a subject, a tissue, or a cell, and preferably in an animal, more preferably in a mammal, without undue adverse side effects (such as toxicity, irritation, or allergic response), commensurate with a reasonable benefit/risk ratio, when used in the manner of this invention. The specific "safe and therapeutically effective amount" will, obviously, vary with such factors as the particular condition being treated, the physical condition of the patient, the duration of treatment, the nature of concurrent therapy (if any), the specific dosage form to be used, the carrier employed, the solubility of the compound therein, and the dosage regimen desired for the composition.

The composition useful for the present invention contains the selected compound which is dispensed in a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the selected compound is to be injected, the preferred pharmaceutically-acceptable carrier is sterile, physiological saline, with blood-compatible suspending agent, the pH of which has been adjusted to about 7.4. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions useful for this invention for parenteral administration, comprises at least about 90% by weight of the total composition.

The compositions useful for this invention are preferably provided in unit dosage form. As used herein, a "unit dosage form" is a composition of this invention containing an amount of a compound that is suitable for administration to an animal, preferably mammal subject, in a single dose, according to good medical practice. (The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. The skilled artisan will recognize that the formulation does not specifically contemplate the entire course of therapy and such decisions are left for those skilled in the art of treatment rather than formulation.) These compositions preferably contain from about 5 mg (milligrams), more preferably from about 10 mg to about 1000 mg, more preferably to about 500 mg, most preferably to about 300 mg, of the selected compound.

The compositions useful for this invention may be in any of a variety of forms, suitable (for example) for oral, nasal, rectal, topical (including transdermal), ocular, intracereberally, intravenous, intramuscular, or parenteral administration. (The skilled artisan will appreciate that oral and nasal compositions comprise compositions that are administered by inhalation, and made using available methodologies.) Depending upon the particular route of administration desired, a variety of pharmaceutically-acceptable carriers well-known in the art may be used. These include solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as miagnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions useful for this invention can also be administered topically to a subject, e.g., by the direct application or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the compound. Suitable carriers for topical administration preferably remain in place on the skin as a continuous film, and resist being removed by perspiration or immersion in water. Generally, the carrier is organic in nature and capable of having dispersed or dissolved therein the compound. The carrier may include pharmaceutically-acceptable emollients, emulsifiers, thickening agents, solvents and the like.

Methods of Administration

According to the present invention, the compounds and the compositions thereof can be administered topically or systemically. Systemic application includes any method of introducing compound into the tissues of the body, e.g., intra-articular, intrathecal, epidural, intramuscular, transdermal, intravenous, intraperitoneal, subcutaneous, sublingual administration, inhalation, rectal, or oral administration. Oral administration is preferred in the present invention.

The specific dosage of the compound to be administered, as well as the duration of treatment is to be individualised by the treating clinicians. Typically, for a human adult (weighing approximately 70 kilograms), from about 5 mg, preferably from about 10 mg to about 3000 mg, more preferably to about 1000 mg, more preferably to about 300 mg, of the selected compound is administered per day. It is understood that these dosage ranges are by way of example only, and that daily administration can be adjusted depending on the factors listed above.

In all of the foregoing, of course, the selected compound can be administered alone or as mixtures, and the compositions may further include additional drugs or excipients as appropriate for the indication. For example, in the treatment of cardiovascular diseases, it is clearly contemplated that the invention may be used in conjunction with beta-blockers, calcium antagonists, ACE inhibitors, diuretics, angiotensin receptor inhibitors, or known cardiovascular drugs or therapies. Hence, in this example, the compositions of this invention are useful when dosed together with another active and can be combined in a single dosage form or composition.

The compositions can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Preparation of Compounds of the Invention

The starting materials used in preparing the compounds useful for this invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, $2^{nd}$ Ed., John Wiley & Sons (1991).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure.

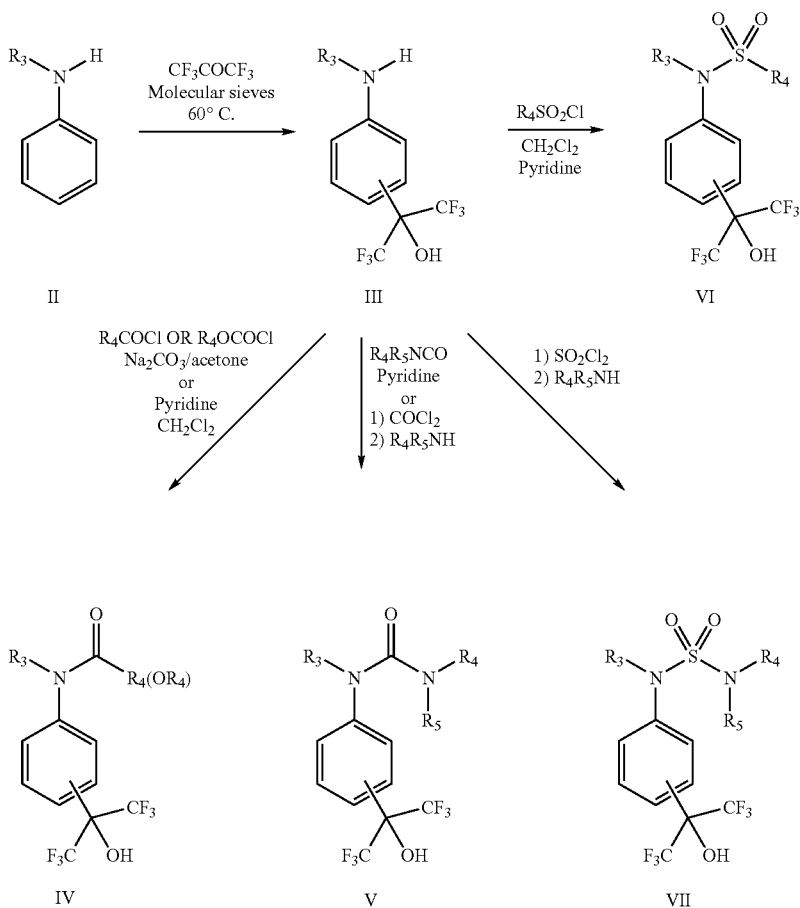

As shown in Scheme 1, aniline derivative II, which either is commercially available or prepared easily via literature procedure, is converted into its corresponding N-substituted phenylhexafluoroisopropanol aniline derivatives III. The latter is transformed into the corresponding amide/carbamates (IV), urea V, sulfonamide (VI) and sulfamides (VII) according to the literature procedures as shown in the above scheme.

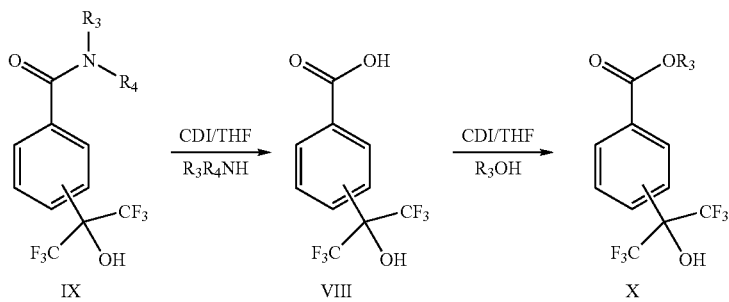

Similarly, the commercially available benzoic acid derivative VIII is converted into its corresponding amides (IX) or esters (X) using the literature procedures as shown in Scheme 2.

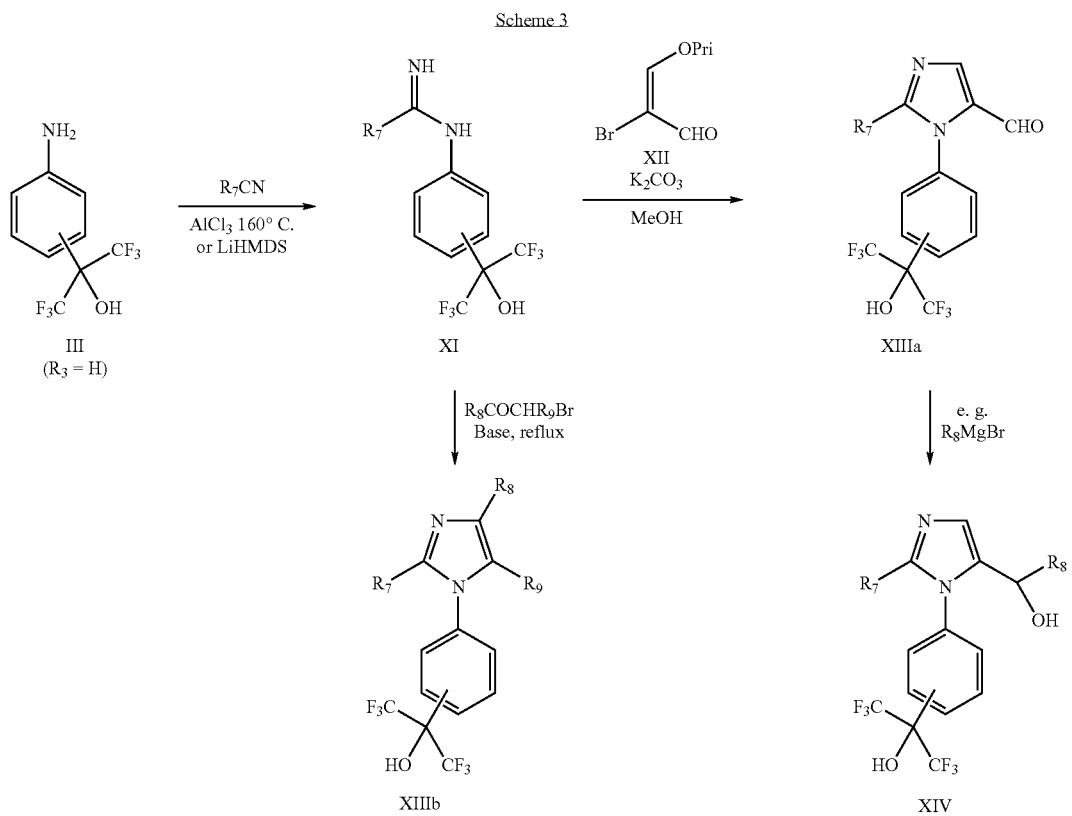

As shown in Scheme 3, imidazole derivatives are prepared from an amidine intermediate XI which in turn is prepared from the aniline derivatives and nitriles in the presence of a Lewis acid at elevated temperature or in the presence of a strong base such as lithium hexamethyldisilyl amide. In the next step, the amidine is treated with an activated α-haloketone or α-haloaldehyde to give the desired imidazole ring system. The resulting imidazole compounds, for example, XIIIa and XIIIb, are further modified to give other derivatives such as compounds XIV.

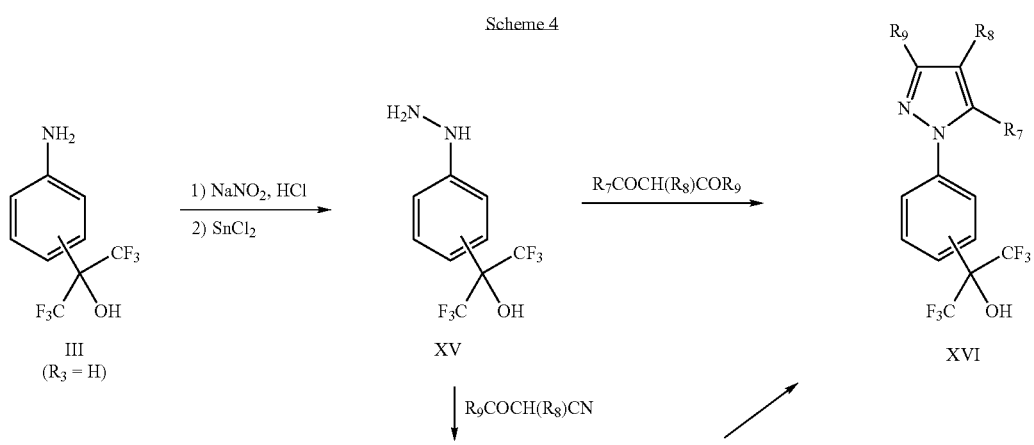

-continued

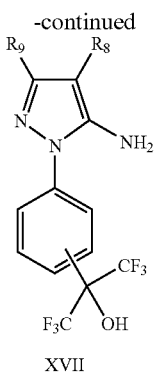

XVII

The aniline derivative III is converted into its corresponding hydrazine XV, which is reacted with diketones to give the substituted pyrazoles XVI in good yield. Alternatively, the reaction of the hydrazine XV with β-cyanoketone results in 5-aminopyrazoles XVII, which is then converted to give the pyrazole derivatives XVI.

Biological Activity

In Vitro MCD Inhibitory Assay:

A spectrophotometric method for the determination of malonyl-CoA decarboxylase activity assay described in the literature, is adapted and modified for MCD inhibitory activity assay in a high-throughput format (Kolattukudy et al., *Methods in Enzymology* 71:150(1981)). The following reagents are added into a 96 well titer plate: Tris-HCl buffer, 20 μL; DTE, 10 μL; I-malate, 20 μL; NAD, 10 μL; NADH, 25 μL; water, 80 μL; malic dehydrogenase, 5 μL. The contents are mixed and incubated for 2 min followed by the addition of 5 μL of citrate synthase. The compound is added followed by 5 μL of malonyl-CoA decarboxylase prepared from rat heart and 20 μL of malonyl-CoA. The content is incubated and absorbence at 460 nM is measured.

Active compounds are characterized by the concentration of the compound that caused 50% inhibition of MCD activity ($IC_{50}$). The preferred compounds have the $IC_{50}$ value less than 10 μM. The most preferred compounds have the $IC_{50}$ value less than 100 nM.

TABLE I $IC_{50}$ of the MCD inhibitors

| Compound | $IC_{50}$ (μM) |
|---|---|
| Example 1-3 | 0.007 |
| Example 2-5 | 0.604 |
| Example 4-94 | 0.009 |
| Example 4-114 | 0.01 |
| Example 4-130 | 0.036 |
| Example 6-1 | 0.018 |
| Example 6-3 | 0.037 |
| Example 6-4 | 0.041 |
| Example 7-1 | 0.067 |
| Example 8-4 | 0.557 |
| Example 8-28 | 0.223 |

Glucose Oxidation and Fatty Acid Oxidation Measurement in the Perfused Rat Heart:

Isolated working hearts from male Sprague-Dawley rats are subjected to a 60-minute aerobic perfusion period with a modified Krebs-Henseleit solution containing 5 mmol/L glucose; 100 μU/mL insulin; 3% BAS; and 1.2 mmol/L palmitate. Working hearts are used in these studies to approximate the metabolic demand of the heart seen in vivo. (Kantor et al., *Circulation Research* 86:580-588(2000)). The test compound is added 5 minutes into the perfusion period.

Glucose oxidation rates are determined by the quantitative collection of $^{14}CO_2$ produced by hearts perfused with buffer containing [U14]-Glucose. Rates of fatty acid oxidation are determined by the quantitative collection of $^{14}CO_2$ produced by hearts perfused with buffer containing [$^{14}C$]palmitate (McNeill, J. H. in "*Measurement of cardiovascular function*", chapter 2, CRC press, New York (1997)).

Active compounds are characterized by an increase in glucose oxidation as compared to control experiment (DMSO). The compounds that caused statistically significant increases in glucose oxidation are considered to be active. The preferred compounds cause statistically significant increases in glucose oxidation at 20 μM. Statistical significance was calculated using the Student's t test for paired or unpaired samples, as appropriate. The results with P<0.05 are considered to be statistically significant.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1H$ nuclear magnetic resonance spectra (NMR) is measured in $CDCl_3$ or other indicated solvents on a Varian NMR spectrometer (Unity Plus 400, 400 MHz for $^1H$) unless otherwise indicated and peak positions are expressed in parts per million (ppm) downfield from tetramethylsilane. The peak multiplicities are denoted as follows, s, singlet; d, doublet; t, triplet; m, multiplet.

The following abbreviations have the indicated meanings:
Ac=acetyl
Allyl=CH$_2$=CH$_2$—CH$_2$—
Bn=benzyl
CDI=carbonyl diimidazole
CH$_2$Cl$_2$=dichloromethane
DIBAL=diisobutylaluminum hydride
DMAP=4-(dimethylamino)-pyridine
DMF=N,N-dimethylformamide
DMSO=dimethylsulfoxide
EDCl or EDAC=1-[3-(dimethylamino)propyl]-3-ethyl-carbodiimide hydrochloric acid
ESIMS=electron spray mass spectrometry
Et$_3$N=triethylamine
EtOAc=ethyl acetate
HMTA=hexamethylenetetramine
Lawesson's reagent=2,4-bis(4-methoxyphenyl)-1,3,2,4-dithiadiphosphetane-2,4-disulfide
LDA=lithium diisopropylamide
LHMDS=lithium bis(trimethylsilyl)amide
MgSO$_4$=magnesium sulfate
NaHCO$_3$=sodium bicarbonate
Na$_2$CO$_3$=sodium carbonate
NaH=sodium hydride
NBS=N-bromosuccinimide
NCS=N-chlorosuccinimide
NH$_4$Cl=ammonium chloride
Ph=phenyl
Py=pyridinyl
r.t.=room temperature
TFA=trifluoroacetic acid
THF=tetrahydrofuran
TLC=thin layer chromatography
TMS=trimethylsilyl
Tf$_2$O=triflic anhydride
Vinyl=CH$_2$=CH—
Alkyl group abbreviations
Me=methyl
Et=ethyl
n-Pr=normal propyl
i-Pr=isopropyl
n-Bu=normal butyl
c-Hexyl=cyclohexyl Example 1

Preparation of N-ethyl-2-methyl-N-{4-[2,2,2-trifluoro-1-hydroxy-1-(trifluoromethyl)ethyl]-phenyl}propanamide

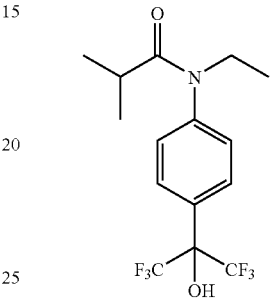

2-(p-N-Ethylphenyl)-hexafluoroisopropanol (172.3 mg, 0.6 mmol) and poly(4-vinylpyridine) (204.5 mg, 1.8 mmol) are mixed in CH$_2$Cl$_2$ (3 mL). Isobutyryl chloride (62.8 μL, 0.6 mmol) is added to the suspension and the reaction mixture is stirred at room temperature for 14 hrs. The polymer is removed by filtration through a pad of Celite and the organic solvent is removed under reduced pressure. The residue is purified by preparative TLC (Hexane:EtOAc, 7:3) to afford the title compound as white solid (87 mg, 41%). $^1$H NMR δ0.99 (d, 6H), 1.09 (t, 3H), 2.40 (m, 1H), 3.71 (q, 2H), 7.37 (d, 2H), 7.84 (d, 2H); ESIMS: m/z 358 (M+H).

TABLE 1

The following compounds are prepared in accordance with the procedure described as in the above example.

| Example | R$_4$ | R$_3$ |
| --- | --- | --- |
| Example 1-1 | 3-Indolyl-CO— | —Me |
| Example 1-2 | i-Pr— | (Et)$_2$NCH$_2$CH$_2$— |
| Example 1-3 | p-pyridinyl- | HOOC(CH$_2$)$_4$— |
| Example 1-4 | i-Pr— | 5-Tetrazolyl-CH$_2$CH$_2$CH$_2$CH$_2$— |
| Example 1-5 | i-Pr— | HOOC(CH$_2$)$_4$— |
| Example 1-6 | p-CN—Ph— | -nBu |
| Example 1-7 | i-Pr— | CN—CH$_2$CH$_2$CH$_2$CH$_2$— |
| Example 1-8 | i-Pr— | -nBu |
| Example 1-9 | Me$_2$(OH)C— | HOOC(CH$_2$)$_4$— |
| Example 1-10 | i-Pr— | MeO$_2$C(CH$_2$)$_4$— |

TABLE 1-continued

The following compounds are prepared in accordance with the procedure described as in the above example.

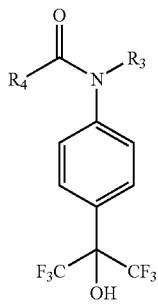

| Example | R₄ | R₃ |
|---|---|---|
| Example 1-11 | p-pyridinyl- | -nBu |
| Example 1-12 | i-Pr— | -nPr |
| Example 1-13 | n-Bu—CH(Et)— | —Et |
| Example 1-14 | -2-Py | -nBu |
| Example 1-15 | i-Pr— | MeO₂CCH₂— |
| Example 1-16 | p-CN—Ph— | —Et |
| Example 1-17 | i-Pr— | -Allyl |
| Example 1-18 | (Et)₂CH— | —Et |
| Exam le 1-19 | i-Pr— | —Et |
| Example 1-20 | p-pyridinyl- | MeO₂C(CH₂)₄— |
| Example 1-21 | -nBu | —Et |
| Example 1-22 | Me₂(OH)C— | -nBu |
| Example 1-23 | (Me)₂C=CH— | -nPr |
| Example 1-24 | nPrCH(Me)— | —Et |
| Example 1-25 | c-Cyclobutanyl- | —Et |
| Example 1-26 | —Et | —Et |
| Example 1-27 | n-Penlyl- | —Et |
| Example 1-28 | c-Pr— | —Et |
| Example 1-29 | PhCH(Et)— | —Et |
| Example 1-30 | -Cyclohex | —Et |
| Example 1-31 | PhCH₂CH₂— | -nBu |
| Example 1-32 | i-Pr— | HOOC—(CH₂)₅NHCOCH(Et)— |
| Example 1-33 | Me₂(OH)C— | MeO₂C(CH₂)₄— |
| Example 1-34 | p-pyridinyl- | —Et |
| Example 1-35 | n-Hexyl— | —Et |
| Example 1-36 | i-PrCH₂CH₂— | —Et |
| Example 1-37 | —Et | MeO₂CCH₂— |
| Example 1-38 | PhCH₂CH₂— | MeO₂CCH₂— |
| Example 1-39 | EtCONHCH₂— | —Et |
| Example 1-40 | i-Pr— | —CH₂CH₂OH |
| Example 1-41 | -2-Py | —Et |
| Example 1-42 | i-Pr— | p-HOPhCH₂CH₂NHCOCH(iBu)— |
| Example 1-43 | p-pyridinyl- | p-HOPhCH₂CH₂NHCOCH(iPr)— |
| Example 1-44 | (Et)₂N + CH(Me)— | —Et |
| Example 1-45 | PhCH₂CH₂— | -Cyclohexyl |
| Example 1-46 | PhCH₂CH₂CH₂— | —Et |
| Example 1-47 | t-BuCH₂— | —Me |
| Example 1-48 | PhCH₂CH₂— | —Et |
| Example 1-49 | p-CN—Ph— | —Me |
| Example 1-50 | (Et)₂NCH(Me)— | —Et |
| Example 1-51 | i-Pr— | —Me |
| Example 1-52 | MeCH=CH— | —Et |
| Example 1-53 | i-BuN(Me)CH₂— | —Et |
| Example 1-54 | BnN + (Me)CH₂— | —Et |
| Example 1-55 | HOCH₂CH₂N(Et)CH₂— | —Et |
| Example 1-56 | PhCH₂CH₂— | i-Pr— |
| Example 1-57 | Me₂(OH)C— | —Et |
| Example 1-58 | o-Cl—Ph— | —Me |
| Example 1-59 | BnN(Me)CH₂— | —Et |
| Example 1-60 | i-Pr— | HOOC(CH₂)₅NHCOCH(iPr)— |
| Example 1-61 | o-MeOPh— | —Et |
| Example 1-62 | PhCH(Et)— | —Me |
| Example 1-63 | HOOCC(Me)₂CH₂— | —Et |
| Example 1-64 | —Et | —Me |
| Example 1-65 | o-l-Ph | —Me |
| Example 1-66 | c-Pr— | —Me |
| Example 1-67 | m-Me₂N—Ph— | —Me |
| Exam le 1-68 | p-CN—Ph—CONHCH₂— | —Et |

TABLE 1-continued

The following compounds are prepared in accordance with the procedure described as in the above example.

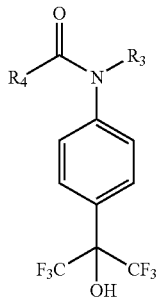

| Example | R₄ | R₃ |
| --- | --- | --- |
| Example 1-69 | m-CN—Ph— | —Me |
| Example 1-70 | o-CF₃—Ph— | —Me |
| Example 1-71 | PhCH₂CH₂— | HOOCCH₂— |
| Example 1-72 | p-pyridinyl- | —Me |
| Example 1-73 | PhOCH₂CH₂CH₂— | —Me |
| Example 1-74 | PhOCH(Me)— | —Me |
| Example 1-75 | -Bn | —Me |
| Example 1-76 | 2-Benzopyrazinyl | —Me |
| Example 1-77 | 2-Naphthyl- | —Me |
| Example 1-78 | 2-Theinyl-CH₂— | —Me |
| Example 1-79 | 4-Py—SCH₂— | —Me |
| Example 1-80 | c-pentylCH₂CH₂— | —Me |
| Example 1-81 | PhCH₂CH₂CH₂— | —Me |
| Example 1-82 | p—EtOPh— | —Me |
| Example 1-83 | (Et)₂NCH₂— | —Et |
| Example 1-84 | PhCH₂CH₂— | -Bn |
| Example 1-85 | i-Pr— | HOOCCH₂— |
| Example 1-86 | MeOCH₂— | —Me |
| Example 1-87 | o-Tolyl- | —Me |
| Example 1-88 | (Et)₂N + CH₂— | —Et |
| Example 1-89 | PhSCH₂— | —Me |
| Example 1-90 | 3,4-dimethoxyphenyl-CH₂CH₂— | —Me |
| Example 1-91 | p-MeOPh— | —Me |
| Example 1-92 | PhCH₂OCH₂— | —Me |
| Example 1-93 | o-MeOPh— | —Me |
| Example 1-94 | PhCH₂CH₂— | —Me |
| Example 1-95 | p-CF₃Ph— | —Me |
| Example 1-96 | p-ClPhO—C(Me)₂— | —Me |
| Example 1-97 | —Et | HOOCCH₂— |
| Example 1-98 | Ph-c(CHCH₂CH)— | —Me |
| Example 1-99 | p-MeOPhCH₂CH₂— | —Me |
| Example 1-100 | 5-Methyl-3-oxazolyl- | —Me |
| Example 1-101 | PhCH=CH— | —Me |
| Example 1-102 | 4-Py—CH₂— | —Me |
| Example 1-103 | HOOC-c(CHCH₂CH)— | —Et |
| Example 1-104 | -3-Py | —Me |
| Example 1-105 | Biphenyl | —Me |
| Example 1-106 | m-ClPh— | —Me |
| Example 1-107 | 2-furyl | —Me |
| Example 1-108 | 2-HOOC-cyclohexyl | —Et |
| Example 1-109 | -nPr | —Me |
| Example 1-110 | 3,4,5-trimethoxyphenyl | —Me |
| Example 1-111 | —CO₂Et | —Me |
| Example 1-112 | PhCH₂CH₂CH₂CH₂— | —Me |
| Example 1-113 | PhCH₂CH₂— | —Me |
| Example 1-114 | i-Pr— | CH₂=CHCH₂— |
| Example 1-115 | HOOCC(Me)₂CH₂CH₂— | —H |
| Example 1-116 | PhOCH(Me)— | —H |
| Example 1-117 | p-(n-Bu)-Ph— | —Me |
| Example 1-118 | PhCH₂CH₂— | —Me |

Example 2

Preparation of 1-diethylaminosulfonylamino-4-[2,2,2-trifluoro-1-hydroxy-1-(trifluoromethyl)ethyl]-benzene

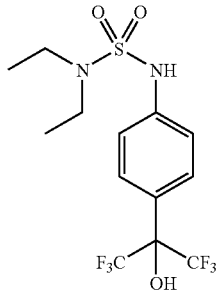

2-(p-Aminophenyl)-hexafluoroisopropanol (50 mg 0.193 mmol) and DMAP (23.6 mg, 0.193 mmol) are dissolved in $CH_2Cl_2$ (5 mL) and added dropwise to the sulphuryl chloride solution (130 mg, 0.965 mmol) in $CH_2Cl_2$ (5 mL) at $-78°$ C. After the reaction mixture is stirred at $-78°$ C. for 15 min, diethylamine (282 mg 3.86 mmol) solution in $CH_2Cl_2$ (5 mL) is introduced. The reaction mixture is stirred at $-78°$ C. for another 1 hr. The cooling bath is removed and the reaction mixture is allowed to warm to room temperature. After stirring for 1 hr, saturated aqueous $NaHCO_3$ is added, and the mixture is extracted with $CH_2Cl_2$. The combined organic solvent is washed with water, dilute aqueous HCl, water, and brine. The dried ($Na_2SO_4$) organic solvent is removed under reduced pressure. The residue is purified by preparative TLC ($CH_2Cl_2$:MeOH, 10:1) and further by preparative RP-HPLC (solvent system of 40% acetonitrile in water with 0.1% TFA to 90% acetonitrile in water with 0.1% TFA over 20 min) to afford the title compound as colorless solid (10.7 mg, 14%). $^1$H NMR $\delta$1.03 (t, 6H), 3.26 (q, 4H), 7.19 (d, 2H), 7.61 (d, 2H); ESIMS: m/z 393 (M–H).

TABLE 2

The following compounds are prepared in accordance with the procedure described as in the above example.

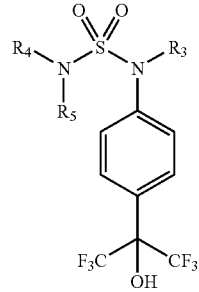

| Example | $R_4$ | $R_5$ | $R_3$ |
|---|---|---|---|
| Example 2-1 | —H | t-BuOCO— | —H |
| Example 2-2 | —H | p-HO(CF$_3$)$_2$C—Ph— | —H |
| Example 2-3 | —H | -nPr | —H |
| Example 2-4 | —Et | —Et | —H |
| Example 2-5 | —(CH$_2$)$_5$— | | —H |
| Example 2-6 | —H | -Bn | —H |
| Example 2-7 | —H | -Cyclohexyl | c-Hexyl—NHSO$_2$— |
| Example 2-8 | —H | (Ph)$_2$CH— | —H |
| Example 2-9 | —H | 4-Biphenylmethyl | —H |
| Example 2-10 | —H | —H | —H |
| Example 2-11 | —H | n-Pentyl- | —H |
| Example 2-12 | —H | i-PrCH$_2$CH$_2$— | —H |
| Example 2-13 | —H | i-PrCH$_2$CH$_2$— | —Me |
| Example 2-14 | -iBu | -iBu | —H |
| Example 2-15 | i-PrCH$_2$CH$_2$— | i-PrCH$_2$CH$_2$— | —H |

Example 3

Preparation of N-benzyl-N'-{4-[2,2,2-trifluoro-1-hydroxy-1-(trifluoromethyl)ethyl]phenyl}urea

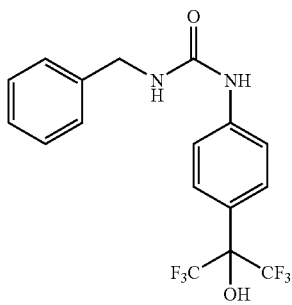

Into a 4 mL vial is added 2-(4-aminophenyl)-1,1,1,3,3,3-hexafluoro-2-propanol (75 mg, 0.289 mmol), anhydrous pyridine (1 mL) and benzyl isocyanate (0.036 mL, 0.289 mmol). The reaction mixture was stirred at r.t. for 2 days. To the reaction mixture is added H$_2$O to precipitate the product. The solid is filtered and purified by preparative TLC (MeOH/CHCl$_3$ 10:90) to give a colorless solid (84.3 mg, 75%). m.p. 163-164° C. (dec). $^1$H NMR (DMSO & CHCl$_3$) 4.23 (d, 2H), 6.05 (t, 1H), 7.05 (m, 1H), 7.08 (m, 4H), 7.25 (t, 3H), 7.42 (d, 2H), 8.02 (s, 1H); ESIMS: m/z 393 (M+H).

Example 4

Preparation of N-methyl-N-{4-[2,2,2-trifluoro-1-hydroxy-1-(trifluoromethyl)ethyl]phenyl}morpholine-4-carboxamide

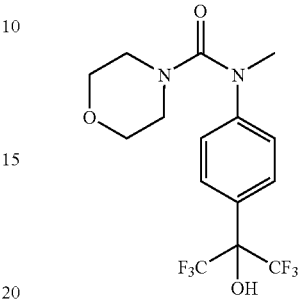

2-(p-N-Methylphenyl)-hexafluoroisopropanol (68 mg, 0.25 mmol) and poly(4-vinylpyridine) (150 mg) are mixed in CH$_2$Cl$_2$ (3 mL). Morpholinyl chloride (0.5 mmol) is and the reaction mixture is stirred at room temperature for 14 hrs. The polymer is removed by filtration through a pad of Celite® and the organic solvent is removed under reduced pressure. The residue is crystallized from CH$_2$Cl$_2$ to afford the title compound as colorless crystal (30 mg). $^1$H NMR δ3.07 (t, 4H), 3.45 (t, 4H), 3.70 (s, 3H), 4.10 (s, 1H), 7.10 (d, 2H), 7.65 (d, 2H); ESMIS: m/z 387 (M+H).

TABLE 3

The following compounds are prepared in accordance with the procedure described as in the above example.

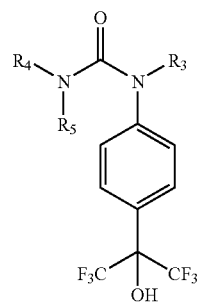

| Example | R$_4$ | R$_5$ | R$_3$ |
|---|---|---|---|
| Example 4-1 | —Et | Ph— | —Me |
| Example 4-2 | —Me | Bn- | —Me |
| Example 4-3 | —Me | Bn- | —Et |
| Example 4-4 | —H | 2-F-4-Br—Ph— | —Me |
| Example 4-5 | —H | 2,6-difluoro-Ph— | —Me |
| Example 4-6 | —H | 2,6-dimethoxy-Ph— | —Me |
| Example 4-7 | —Et | Ph— | —Et |
| Example 4-8 | —Me | Ph— | —Et |
| Example 4-9 | -Allyl | Ph— | —Et |
| Example 4-10 | -nBu | Ph— | —Et |
| Example 4-11 | -Bn | Ph— | —Et |
| Example 4-12 | —H | 4-Br-2,6-dimethyl-Ph— | —Me |
| Example 4-13 | CN—CH$_2$CH$_2$- | Ph— | —Et |
| Example 4-14 | —Me | PhCH$_2$CH$_2$— | —Et |
| Example 4-15 | —Me | p—MeO$_2$CPh— | —Et |
| Example 4-16 | —CH$_2$CH$_2$OCH$_2$CH$_2$— | | —Et |
| Example 4-17 | —CH$_2$CH$_2$CH(Bn)CH$_2$CH$_2$— | | —Et |

TABLE 3-continued

The following compounds are prepared in accordance with the procedure described as in the above example.

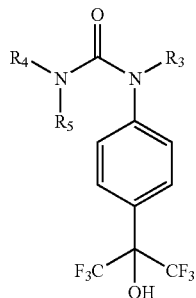

| Example | R₄ | R₅ | R₃ |
|---|---|---|---|
| Example 4-18 | —Et | —CH₂CH₂OH | —Et |
| Example 4-19 | —Et | CN—CH₂CH₂— | —Et |
| Example 4-20 | —(CH₂)₅— | | —Et |
| Example 4-21 | —(CH₂)₄— | | —Et |
| Example 4-22 | -nPr | c-Pr-CH₂— | —Et |
| Example 4-23 | —Me | iBu— | —Et |
| Example 4-24 | -iBu | lBu- | —Et |
| Example 4-25 | —Et | Cyclohexyl- | —Et |
| Example 4-26 | -iBu | m-NO₂PhCOOCH₂CH₂— | —Et |
| Example 4-27 | —Et | HO(CH₂)₄— | —Et |
| Example 4-28 | —Et | MeOCH₂CH₂— | —Et |
| Example 4-29 | —Et | Me₂NCH₂CH₂— | —Et |
| Example 4-30 | 4-Cl-6-Me—PhCH₂CH₂— | c-Pr—CH₂— | —Et |
| Example 4-31 | —Et | MeC(OH)(Me)CH₂— | —Et |
| Example 4-32 | -Bn | -2-Py | —Et |
| Example 4-33 | —Me | —Me | —Et |
| Example 4-34 | —Me | -nPr | —Et |
| Example 4-35 | —Et | —Et | —Et |
| Example 4-36 | —H | 1-Piperidinyl- | —Et |
| Example 4-37 | —H | Ph—N(Me)— | —Et |
| Example 4-38 | —Et | p-HO(CF₃)₂C—Ph— | —Et |
| Example 4-39 | —CH₂CH₂OH | —CH₂CH₂OH | —Et |
| Example 4-40 | —Me | —Me | -nPr |
| Example 4-41 | —Me | -nPr | -nPr |
| Example 4-42 | —Et | —Et | -nPr |
| Example 4-43 | —H | —NMe₂ | -nPr |
| Example 4-44 | —(CH₂)₅— | | -nPr |
| Example 4-45 | —H | 1-Piperidinyl- | -nPr |
| Example 4-46 | —CH₂CH₂OCH₂CH₂— | | -nPr |
| Example 4-47 | —Et | HO(CH₂)₄— | -nPr |
| Example 4-48 | —CH₂CH₂OCH₂CH₂— | | —CH₂CH₂OH |
| Example 4-49 | —CH₂CH₂OH | HOCH₂CH₂CH₂— | -nPr |
| Example 4-50 | —CH₂CH₂OH | 1-Morpholinyl-CH₂CH₂— | -nPr |
| Example 4-51 | EtO₂CCH₂— | EtO₂CCH₂— | -nPr |
| Example 4-52 | —Et | —CH₂CONH₂ | -nPr |
| Example 4-53 | CN—CH₂CH₂— | 1-Morpholinyl-CH₂CH₂CH₂— | -nPr |
| Example 4-54 | Me₂NCH₂CH₂CH₂— | Me₂NCH₂CH₂CH₂— | -nPr |
| Example 4-55 | —CH₂CH₂OCH₂CH₂— | | —H |
| Example 4-56 | —CH₂CH₂OCH₂CH₂— | | n-Pentyl- |
| Example 4-57 | —CH₂CH₂OCH₂CH₂— | | n-Hexyl— |
| Example 4-58 | —CH₂CH₂OCH₂CH₂— | | n-Haptyl— |
| Example 4-59 | Me₂N(+)CH₂CH₂CH₂— | | -nPr |
| Example 4-60 | —Et | HO(CH₂)₄— | -nBu |
| Example 4-61 | —CH₂CH₂OCH₂CH₂— | | -nBu |
| Example 4-62 | —CH₂CH₂OH | 1-Morpholinyl-CH₂CH₂— | -nBu |
| Example 4-63 | EtO₂CCH₂— | EtO₂CCH₂— | -nBu |
| Example 4-64 | —Et | —CH₂CONH₂ | -nBu |
| Example 4-65 | CN—CH₂Ch₂— | 1-Morpholinyl-CH₂CH₂CH₂— | -nBu |
| Example 4-66 | —CH₂CH₂OCH₂CH₂— | | n-Octyl |
| Example 4-67 | —CH₂CH₂OCH₂CH₂— | | i-PrCH₂CH₂— |
| Example 4-68 | —CH₂CH₂OH | HOCH₂CH₂CH₂— | -nBu |
| Example 4-69 | —CH₂CH₂OCH₂CH₂— | | c-Hexyl—CH₂CH₂— |

TABLE 3-continued

The following compounds are prepared in accordance with the procedure described as in the above example.

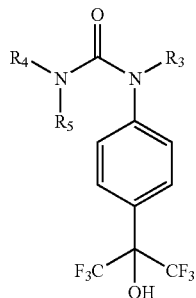

| Example | R₄ | R₅ | R₃ |
|---|---|---|---|
| Example 4-70 | —CH₂CH₂OCH₂CH₂— | | CN(CH₂)₃— |
| Example 4-71 | —CH₂CH₂OCH₂CH₂— | | AcO(CH₂)₄— |
| Example 4-72 | —CH₂CH₂OCH₂CH₂— | | MeO₂C(CH₂)₄— |
| Example 4-73 | —CH₂CH₂OCH₂CH₂— | | HO(CH₂)₄— |
| Example 4-74 | —CH₂CH₂OCH₂CH₂— | | HOOC(CH₂)₄— |
| Example 4-75 | —Me | —Me | -nBu |
| Example 4-76 | —Et | —Et | -nBu |
| Example 4-77 | —(CH₂)₄— | | -nBu |
| Example 4-78 | —CH₂CH₂OCH₂CH₂— | | EtO₂C(CH₂)₂— |
| Example 4-79 | —CH₂CH₂OCH₂CH₂— | | PhCH₂CH₂— |
| Example 4-80 | —CH₂CH₂OH | —CH₂CH₂OH | -nBu |
| Example 4-81 | —Et | -Cyclohex | -nBu |
| Example 4-82 | —Et | HO(CH₂)₄— | MeO₂CCH₂— |
| Example 4-83 | HOOCCH₂— | HOOCCH₂— | -nBu |
| Example 4-84 | —CH₂CH₂OCH₂CH₂— | | MeO₂CCH₂— |
| Example 4-85 | —Et | —CH₂CONH₂ | MeO₂CCH₂— |
| Example 4-86 | —Me | —Me | MeO₂CCH₂— |
| Example 4-87 | —(CH₂)₄— | | MeO₂C(CH₂)₄— |
| Example 4-88 | —Et | —Et | MeO₂C(CH₂)₄— |
| Example 4-89 | —Et | CN—CH₂CH₂— | MeO₂C(CH₂)₄— |
| Example 4-90 | —Et | HO(CH₂)₄— | MeO₂C(CH₂)₄— |
| Example 4-91 | —Et | -Cyclohex | MeO₂C(CH₂)₄— |
| Example 4-92 | —(CH₂)₄— | | HOOC(CH₂)₄— |
| Example 4-93 | —Et | —Et | HOOC(CH₂)₄— |
| Example 4-94 | —Et | CN—CH₂CH₂— | HOOC(CH₂)₄— |
| Example 4-95 | —Et | HO(CH₂)₄— | HOOC(CH₂)₄— |
| Example 4-96 | —Et | -Cyclohexyl | HOOC(CH₂)₄— |
| Example 4-97 | —Et | HO(CH₂)₄— | EtO₂C(CH₂)₅— |
| Example 4-98 | —CH₂CH₂OCH₂CH₂— | | EtO₂C(CH₂)₅— |
| Example 4-99 | —CH₂CH₂CH(CH₂CH₂OH)CH₂CH₂— | | -nBu |
| Example 4-100 | —Et | HO(CH₂)₄— | HOOC(CH₂)₅— |
| Example 4-101 | —CH₂CH₂OCH₂CH₂— | | HOOC(CH₂)₅— |
| Example 4-102 | —CH₂CH₂CH(CH₂OH)CH₂CH₂— | | -nBu |
| Example 4-103 | —Me | HO(CH₂)₆— | -nBu |
| Example 4-104 | —Et | HO(CH₂)₄— | EtO₂C(CH₂)₆— |
| Example 4-105 | -nBu | HO(CH₂)₄— | -nBu |
| Example 4-106 | —CH₂CH₂OCH₂CH₂— | | EtO₂C(CH₂)₆— |
| Example 4-107 | —Et | HO(CH₂)₄— | CN—(CH₂)₄— |
| Example 4-108 | —CH₂CH₂OCH₂CH₂— | | CN—(CH₂)₄— |
| Example 4-109 | —Et | HO(CH₂)₄— | HOOC(CH₂)₆— |
| Example 4-110 | —CH₂CH₂OCH₂CH₂— | | HOOC(CH₂)₆— |
| Example 4-111 | —Et | —CH₂CH₂OH | -nBu |
| Example 4-112 | —CH₂CH₂OH | -nPr | -nBu |
| Example 4-113 | —CH₂CH₂CH₂CH(CH₂OH)CH₂— | | -nBu |
| Example 4-114 | —CH₂CH₂OCH₂CH₂— | | 5-Tetrazolyl-CH₂CH₂CH₂CH₂— |
| Example 4-115 | —Me | HOCH₂CH(OH)CH₂— | -nBu |
| Example 4-116 | —CH₂CH₂OCH₂CH₂— | | MeO₂CCH₂CH₂— |
| Example 4-117 | —Et | HO(CH₂)₄— | MeO₂CCH₂CH₂— |
| Example 4-118 | —CH₂CH₂OCH₂CH₂— | | MeO₂C(CH₂)₃— |
| Example 4-119 | —Et | HO(CH₂)₄— | MeO₂C(CH₂)₃— |
| Example 4-120 | —CH₂CH₂OCH₂CH₂— | | HOOCCH₂CH₂— |
| Example 4-121 | —CH₂CH₂OCH₂CH₂— | | HO₂C(CH₂)₃— |
| Example 4-122 | —Et | HO(CH₂)₄— | HOOCCH₂CH₂— |
| Example 4-123 | —Et | HO(CH₂)₄— | HO₂C(CH₂)₃— |
| Example 4-124 | —CH₂CH₂OCH₂CH₂— | | 4-Py—CH₂— |
| Example 4-125 | —CH₂CH₂OCH₂CH₂— | | P—CF3—PhCH₂— |
| Example 4-126 | —CH₂CH₂OCH₂CH₂— | | 3-PyCH₂— |

TABLE 3-continued

The following compounds are prepared in accordance with the procedure described as in the above example.

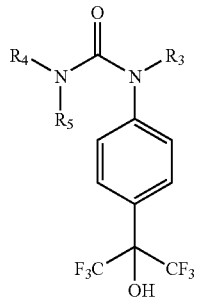

| Example | R₄ | R₅ | R₃ |
|---|---|---|---|
| Example 4-127 | —CH₂CH₂OCH₂CH₂— | | 3-PyCH₂— |
| Example 4-128 | —CH₂CH₂OCH₂CH₂— | | 2-Py—CH₂— |
| Example 4-129 | —CH₂CH₂OCH₂CH₂— | | 2-Py—CH₂— |
| Example 4-130 | —CH₂CH₂OCH₂CH₂— | | FCH₂CH₂CH₂— |
| Example 4-131 | —CH₂CH₂OCH₂CH₂— | | MeC(=CH₂)CH₂— |
| Example 4-132 | —CH₂CH₂OCH₂CH₂— | | 1-PyrrolylCH₂CH₂CH₂— |
| Example 4-133 | —CH₂CH₂OCH₂CH₂— | | t-Bu— |
| | | | C≡CCH=CHCH₂— |
| Example 4-134 | —CH₂CH₂OCH₂CH₂— | | CHCCH₂— |
| Example 4-135 | —CH₂CH₂OCH₂CH₂— | | p-CN-Bn |
| Example 4-136 | —CH₂CH₂OCH₂CH₂— | | MeCCCH₂— |
| Example 4-137 | —CH₂CH₂OCH₂CH₂— | | MeCH₂CCCH₂— |
| Example 4-138 | —CH₂CH₂OCH₂CH₂— | | HON=C(NH₂)—CH₂CH₂CH₂CH₂— |
| Example 4-139 | —CH₂CH₂OCH₂CH₂— | | 3-methyl-5-(1,2,4-oxadiazolyl)(CH₂)₄— |

Example 5

Preparation of 2-[4-(2-pyridinylmethyl-1H-imidazol-1-yl)phenyl]-1,1,1,3,3,3hexafluoro-propan-2-ol

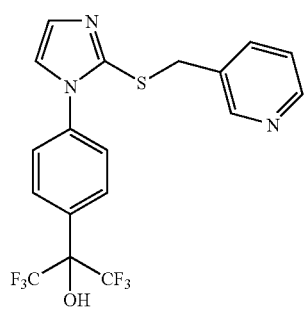

The title compound is obtained in a similar fashion as described above except 3-bromomethyl) pyridine is used instead of benzyl bromide. ¹H NMR δ4.2 (s, 2H), 7.1 (m, 5H), 7.42 (d, 1H), 7.90 (d, 2H), 8.20 (s, 1H), 8.35 (d, 1H); ESIMS: m/z 434 (M+H).

Example 6

Preparation of 1,1,1,3,3,3-hexafluoro-2-{4-[5-(hydroxymethyl)-2-(3-methylpropyl)-1H-imidazol-1-yl]phenyl}propan-2-ol

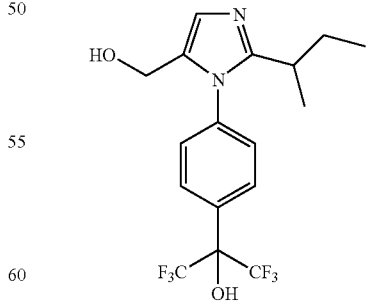

Step 1

Aluminum chloride (3 g, 22.5 mmol) is added to 4-(hexafluoro-2-hydroxyisopropyl)-aniline (3.89 g, 15 mmol) and 2-methylbutyronitrile (15 mL) and heated at 180° C. under argon atmosphere for 14 hours. After cooling the reaction mixture to room temperature, EtOAc is added and subsequently washed with saturated NaHCO$_3$, followed by H$_2$O and brine and dried over MgSO$_4$. EtOAc is removed under reduced pressure and the residue is precipitated with CH$_2$Cl$_2$. The amidine product is filtered and washed with a small amount of CH$_2$Cl$_2$ and dried under vacuum (3.49 g).

Step 2

A solution of 2-bromo-3-(-1-methylethoxy)-2-propenal (2.5 g, 13.1 mmol) and amidine (3 g, 8.76 mmol) obtained above in CHCl$_3$ and water is treated with solid potassium carbonate (1.8 g, 13.1 mmol) at room temperature. The reaction mixture is then heated at 80° C. for 14 hours and diluted with CH$_2$Cl$_2$. The organic layer is separated and washed with H$_2$O and brine and dried over MgSO$_4$. The crude product after removal of solvent is purified by silica gel column chromatography to afford the imidazole aldehyde intermediate (1.3 g).

Step 3

NaBH$_4$ (11.2 mg, 0.296 mmol) is added to a solution of imidazole aldehyde intermediate (116.8 mg, 0.296 mmol) obtained above in MeOH. The reaction mixture is stirred at room temperature for 4 hours. The solvent is removed under reduced pressure and the residue is dissolved in EtOAc. The solution is washed with 1N HCl, saturated NaHCO$_3$, brine and dried over MgSO$_4$. The solvent is removed under reduced pressure and the residue is purified by preparative TLC (CH$_2$Cl$_2$:MeOH, 9:1) to afford the title compound (56.1 mg). $^1$H NMR δ0.75 (t, 3H), 1.20 (d, 3H), 1.51 (m, 1H), 1.72 (m, 1H), 2.42 (m, 1H), 4.34 (q, 2H), 7.00 (s, 1H), 7.51 (d, 2H), 7.95 (d, 2H); ESIMS: m/z 397 (M+H).

TABLE 4

The following compounds are prepared in accordance with the procedure described as in the above examples.

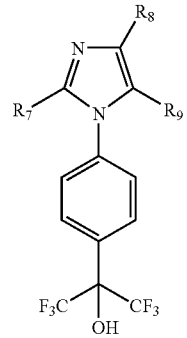

| Example | R$_7$ | R$_8$ | R$_9$ |
|---|---|---|---|
| Example 6-1 | m-CN—PhCH$_2$SO$_2$— | —H | —H |
| Example 6-2 | i-Pr— | —H | CN—CH=CH— |
| Example 6-3 | i-Pr— | —H | EtOCOCH(Me)CH$_2$— |
| Example 6-4 | -sBu | —H | MeO$_2$CCH$_2$CH$_2$— |
| Example 6-5 | i-Pr— | —H | t-BuON=CH— |
| Example 6-6 | i-Pr— | —H | MeOCOCH=CH— |
| Example 6-7 | -sBu | —H | iPrCH(OH)— |
| Example 6-8 | i-Pr— | —H | MeON=CH— |
| Example 6-9 | i-Pr— | —H | MeO$_2$CCH$_2$CH$_2$— |
| Example 6-10 | m-CN—PhCH$_2$— | —H | —H |
| Example 6-11 | -sBu | —H | nPrCH(OH)— |
| Example 6-12 | i-Pr— | —H | HCO— |
| Example 6-13 | -sBu | —H | MeOCOCH=CH— |
| Example 6-14 | i-Pr— | —H | MeON=CH— |
| Example 6-15 | i-Pr— | —H | CN—CH$_2$CH$_2$CH$_2$CH$_2$OCH$_2$— |
| Example 6-16 | p-pyridinyl- | —H | —CH$_2$OH |
| Example 6-17 | i-Pr— | —H | EtOCH—C(Me)=CH— |
| Example 6-18 | i-Pr— | —H | 5-Tetrazolyl CH$_2$CH$_2$CH$_2$CH$_2$OCH$_2$— |
| Example 6-19 | i-Pr— | —H | EtON=CH— |
| Example 6-20 | -iBu | —H | HCO— |
| Example 6-21 | i-Pr— | —H | CN—CH=CH— |
| Example 6-22 | -sBu | —H | EtOCOCH=CH— |
| Example 6-23 | p-pyridinyl- | —H | HCO— |
| Example 6-24 | -sBu | —H | MeCH(OH)— |
| Example 6-25 | i-Pr— | —H | HON=CH— |
| Example 6-26 | i-Pr— | —H | 5-tetrazolyl CH$_2$CH$_2$CH$_2$CH$_2$OCH$_2$— |
| Example 6-27 | -sBu | —H | HOOCCH$_2$CH$_2$— |
| Example 6-28 | i-Pr— | —H | CN—(CH$_2$)$_5$OCH$_2$— |
| Example 6-29 | p-pyridinyl- | —CO$_2$Et | —H |
| Example 6-30 | i-Pr— | —H | EtON=CH— |
| Example 6-31 | i-Pr— | —H | PhON=CH— |

TABLE 4-continued

The following compounds are prepared in accordance with the procedure described as in the above examples.

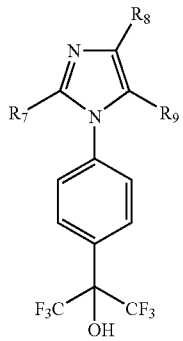

| Example | $R_7$ | $R_8$ | $R_9$ |
|---|---|---|---|
| Example 6-32 | i-Pr— | —H | HOOCCH(Me)CH$_2$— |
| Example 6-33 | i-Pr— | —H | HOOCCH$_2$CH$_2$— |
| Example 6-34 | -sBu | —CH$_2$OH | —H |
| Example 6-35 | -2-Py | —H | HCO— |
| Example 6-36 | i-Pr— | —H | —CH$_2$OH |
| Example 6-37 | -sBu | —H | HCO— |
| Example 6-38 | MeOCH$_2$— | —H | HCO— |
| Example 6-39 | -sBu | —H | nBuNHCH$_2$— |
| Example 6-40 | -sBu | —CO$_2$Et | —H |
| Example 6-41 | -sBu | —H | —CH$_2$OH |
| Example 6-42 | -sBu | —H | MeOCH$_2$CH$_2$NHCH$_2$— |
| Example 6-43 | -sBu | —H | iPrNHCH$_2$— |
| Example 6-44 | EtOCOCH$_2$SCH$_2$— | —H | —H |
| Example 6-45 | i-Pr— | —H | iBuON=CH— |
| Example 6-46 | p-ClPh— | —H | HCO— |
| Example 6-47 | -Bn | —H | HCO— |
| Example 6-48 | BnS— | —H | —H |
| Example 6-49 | BnSO$_2$— | —H | —H |
| Example 6-50 | i-Pr— | —H | iBuON=CH— |
| Example 6-51 | -sBu | —H | PhCH(OH)— |
| Example 6-52 | -sBu | —H | p-F—PhCH(OH)— |
| Example 6-53 | i-Pr— | —H | nBuNHCH$_2$— |
| Example 6-54 | EtOCH$_2$CH$_2$S— | —H | —H |
| Example 6-55 | m-Pyridinyl-CH$_2$S— | —H | —H |
| Example 6-56 | -sBu | —H | HOOC—CH=CH— |
| Example 6-57 | p-pyridinyl- | —CF$_3$ | —H |
| Example 6-58 | m-MePhCH$_2$S— | —H | —H |
| Example 6-59 | -2-Py | —H | —CH$_2$OH |
| Example 6-60 | i-Pr— | —H | t-BuON=CH— |
| Example 6-61 | m-MeOPhCH$_2$S— | —H | —H |
| Example 6-62 | PhCH$_2$CH$_2$S— | —H | —H |
| Example 6-63 | 2-tetrahydropyranylCH$_2$S— | —H | —H |
| Example 6-64 | c-HexylS— | —H | —H |
| Example 6-65 | EtCH(Me)S— | —H | —H |
| Example 6-66 | EtS— | —H | —H |
| Example 6-67 | i-Pr— | —H | PhON=CH— |
| Example 6-68 | nPrS— | —H | —H |
| Example 6-69 | o-MePhCH$_2$S— | —H | —H |
| Example 6-70 | iBuS— | —H | —H |
| Example 6-71 | MeC(=CH$_2$)CH$_2$S— | —H | —H |
| Example 6-72 | p-NO$_2$PhCH$_2$S— | —H | —H |
| Example 6-73 | c-HexylCH$_2$S— | —H | —H |
| Example 6-74 | (Et)$_2$NCH$_2$CH$_2$SO— | —H | —H |

Example 7

Preparation of N-phenethyl-N-methyl4-[2,2,2-trifluoro-1-hydroxy-1-(trifluoromethyl) ethyl]benzamide

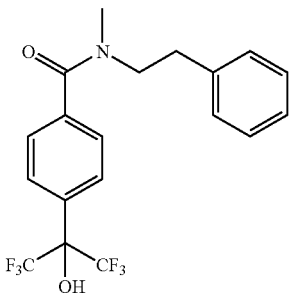

CDI (194.4 mg, 1.2 mmol) is added to the solution of 4-(2-hydroxyhexafluoroisopropyl) benzoic acid (288 mg, 1 mmol) in THF (10 mL) at room temperature. The reaction mixture is stirred for 10 minutes and N-methylphenethylamine (0.174 mL, 1.2 mmol) is introduced. The reaction mixture is then stirred for 14 hours. The solvent is removed and the residue is dissolved in EtOAc. The organic phase is washed with 1N HCl, saturated NaHCO$_3$ and brine and dried over MgSO$_4$. The product is obtained in pure form after removal of solvents (278.8 mg). $^1$H NMR (CD$_3$OD, every peak appears as a pair) δ2.76 (t, 2H), 3.12 (s, 3H), 3.44 (t, 2H), 7.01 (d, 2H), 7.20 (d, 2H), 7.30 (m, 3H), 7.62 (d, 2H); ESIMS: m/z 406 (M+H).

TABLE 5

The following compounds are prepared in accordance with the procedure described as in the above example

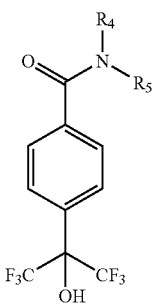

| Example | R$_4$ | R$_5$ |
|---|---|---|
| Example 7-1 | -iBu | -iBu |
| Example 7-2 | c-Pr—CH$_2$— | -nPr |
| Example 7-3 | CN—CH$_2$CH$_2$— | —Et |
| Example 7-4 | MeOCH$_2$CH$_2$— | —Et |
| Example 7-5 | —(CH$_2$)$_4$— | |
| Example 7-6 | —(CH$_2$)$_5$— | |
| Example 7-7 | -Bn | —Me |
| Example 7-8 | —CH$_2$CH$_2$OH | —Et |
| Example 7-9 | —CH$_2$CH$_2$OCH$_2$CH$_2$— | |
| Example 7-10 | —OMe | —Me |
| Example 7-11 | 4-Bn-piperazinyl | |
| Example 7-12 | PhCH$_2$CH$_2$— | —Me |
| Example 7-13 | PhCH$_2$CH$_2$— | —H |
| Example 7-14 | Ph—N(Me)— | —H |

Example 8

Preparation of 5-methyl-1-[4-(2,2,2-trifluoro-1-hydroxy-1-trifluoromethyl-ethyl)phenyl]-1H-pyrazole-3-carboxylic acid ethyl ester

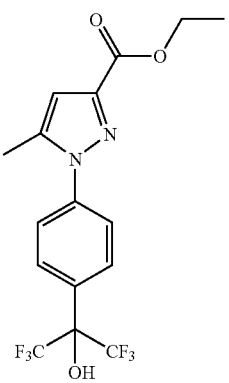

Step 1

A solution of 4-hexafluoro-2-hydroxyisopropylaniline (10.366 g 40 mmol) in 25 ml water plus 12 ml of 37% HCl at 0° C. is treated dropwise with a solution of sodium nitrite (3.036 g 44 mmol) in 8 ml water. After stirring for an additional hour at 0° C., the contents are transferred to a dropping funnel and added dropwise to a vigorously stirred solution of Tin chloride dihydrate (22.5 g 100 mmol) in 100 ml 37% HCl at 0° C. After stirring for an additional hour, the pH of the reaction mixture is adjusted to 7-8 by adding 10N sodium hydroxide with cooling in an ice bath. The milky white aqueous suspension is concentrated and the residue is washed with chloroform-methanol(9:1). The combined organic extracts are dried over MgSO$_4$, and concentrated to obtain 5.9 g hydrazine intermediate as white solid. $^1$H NMR δ 4.9 (m, 2H), 7.59 (d, 2H), 7.82 (s, 1H), 8.14 (d,2H), 9.0 (s, 1H); ESIMS: m/z 275 (M+H)

Step 2

Ethyl 2,4-dioxovalerate (76.8 ul 0.547 mmol) is added to the solution of hydrazine intermediate obtained above in 2 ml ethanol. The reaction mixture is then heated to 80° C. for 12 hours. Then ethanol is removed by vacuum. The reaction mixture is dissolved in EtOAc and washed with Sat. NaHCO$_3$, H$_2$O and brine and dried over MgSO$_4$. Concentration and purification by preparative TLC afford the title compound. $^1$H NMR δ 1.38 (t, 3H), 2.38 (s, 3H), 4.39 (qt, 2H), 6.67 (s, 1H), 7.46 (d, 2H), 7.81 (d, 2H); ESIMS: m/z 395 (M−H)

TABLE 6

The following compounds are prepared in accordance with the procedure described as in the above example.

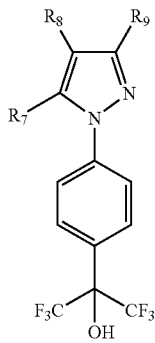

| Example | R₇ | R₈ | R₉ |
|---|---|---|---|
| Example 8-1 | i-Pr— | —H | i-Pr— |
| Example 8-2 | —NH₂ | —H | Ph— |
| Example 8-3 | —NH₂ | Ph— | —Me |
| Example 8-4 | -2-Py | —H | -2-Py |
| Example 8-5 | —NH₂ | Ph— | —CO₂Et |
| Example 8-6 | —NH₂ | —Me | Ph— |
| Example 8-7 | —NH₂ | p-MeOPh— | -Bn |
| Example 8-8 | —NH₂ | EtOCOCH₂CH₂— | —Me |
| Example 8-9 | —NH₂ | —H | p-MeO₂CPh— |
| Example 8-10 | —NH₂ | —H | -tBu |
| Example 8-11 | p-MeOPh— | —H | p-MeOPh— |
| Example 8-12 | —Me | —Me | —Me |
| Example 8-13 | —NH₂ | —H | -2-Thienyl |
| Example 8-14 | —Me | —H | EtOCOCH₂CH₂— |
| Example 8-15 | EtOCOCH₂CH₂— | —H | —Me |
| Example 8-16 | -Bn | —H | —CO₂Et |
| Example 8-17 | —Me | —H | —Me |
| Example 8-18 | HOOCCH₂CH₂CONH— | —H | Ph— |
| Example 8-19 | —NH₂ | —H | p-pyridinyl- |
| Example 8-20 | —Me | —H | —COOH |
| Example 8-21 | —CO₂Et | —H | —Me |
| Example 8-22 | iPrCONH— | —H | p-pyridinyl- |
| Example 8-23 | N-Succinyl | —H | p-pyridinyl- |
| Example 8-24 | HOOCCH₂CH₂CONH— | —H | p-pyridinyl- |
| Example 8-25 | 4-PyridinylCONH— | —H | p-pyridinyl- |
| Example 8-26 | 1-MorpholinylCONH— | —H | p-pyridinyl- |
| Example 8-27 | p-CN—PhCONH— | —H | p-pyridinyl- |
| Example 8-28 | p-pyridinyl- | —H | —Me |
| Example 8-29 | nPrNHCONH— | —H | p-pyridinyl- |
| Example 8-30 | —NH₂ | —H | -3-Py |
| Example 8-31 | p-ClPh—SO₂NH— | —H | p-pyridinyl- |
| Example 8-32 | p-I-PhSO₂NH— | —H | p-pyridinyl- |
| Example 8-33 | -3-Py | —H | —Me |
| Example 8-34 | p-MeO-PhSO₂NH— | —H | p-pyridinyl |

All references described herein are hereby incorporated by reference.

Modification of the preceding embodiments is within the scope of the skilled artisan in formulation, given the guidance of the specification in light of the state of the art.

While particular embodiments of this invention have been described, it will be apparent to those skilled in the art that various changes and modifications of this invention can be made without departing from the spirit and scope of the invention. It is intended to cover, in the appended claims, all such modifications that are within the scope of this invention. Hence, the foregoing written specification is considered to be sufficient to enable one skilled in the art to practice the invention. Indeed, various modifications of the above-described makes for carrying out the invention which are obvious to those skilled in the fields of molecular biology, chemistry, medicine, pharmaceutics, or related fields are intended to be within the scope of the following claims.

What is claimed is:

1. A method for preparing a compound represented by one of structural formulae XIIIa and XIIIb, comprising:

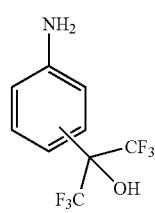

III

-continued

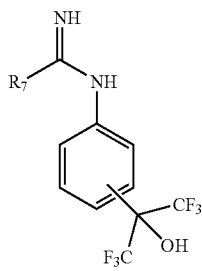
XI

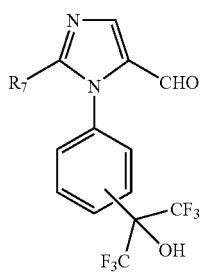
XIIIa

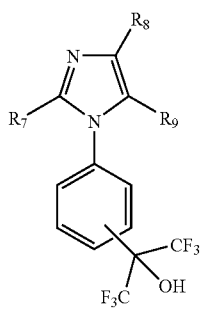
XIIIb forming a compound represented by structural formula XI by treating an aniline derivative represented by structural formula III with $R_7CN$ in the presence of (1) a Lewis acid at elevated temperature or (2) a strong base; and forming the compound represented by one of structural formulae XIIIa and XIIIb by treating the compound represented by structural formula XI with an α-haloketone or an α-haloaldehyde in a solvent, wherein $R_7$, $R_8$, and $R_9$, are independently hydrogen, alkyl, aryl, heterocyclyl, nitro, cyano, carboxylic acid, ester, amide, halo, hydroxyl, amino, substituted amino, alkoxy, acyl, ureido, sulfonamido, sulfamido, sulfonyl, sulfinyl, or guanadinyl.

2. The method of claim 1, wherein the Lewis acid is aluminum chloride.

3. The method of claim 1, wherein the elevated temperature is about 160° C.

4. The method of claim 1, wherein the strong base is lithium hexamethyldisilyl amide.

5. A method for preparing a compound represented by structural formula XIV:

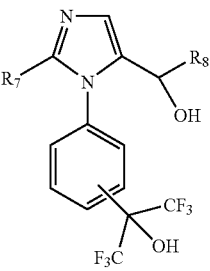
XIV comprising forming a compound represented by structural formula XI by treating an aniline derivative represented by structural formula III with $R_7CN$ in the presence of (1) a Lewis acid at elevated temperature, or (2) a strong base;

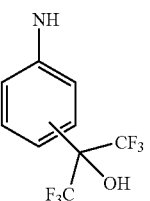
III

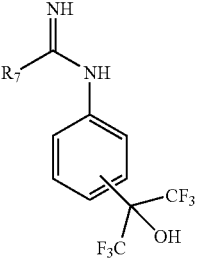
XI forming a compound represented by structural formulae XIIIa by treating the compound represented by structural formula XI with an α-haloaldehyde in a solvent;

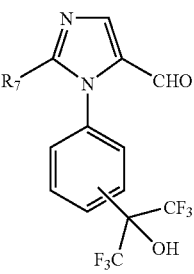
XIIIa forming the compound represented by structural formula XIV by reacting the compound represented by structural formula XIIIa with $NaBH_4$ or $R_8MgBr$, wherein
R₇, is hydrogen, alkyl, aryl, heterocyclyl, nitro, cyano, carboxylic acid, ester, amide, halo, hydroxyl, amino, substituted amino, alkoxy, acyl, ureido, sulfonamido, sulfamido, sulfonyl, sulfinyl, or guanadinyl; and
R₈ is hydrogen, alkyl, aryl, or heterocyclyl.

6. The method of claim 5, wherein the Lewis acid is aluminum chloride.

7. The method of claim 5, the elevated temperature is about 160° C.

8. The method of claim 5, wherein the strong base is lithium hexamethyldisilyl amide.

9. The method of claim 5, wherein the compound represented by structural formula XIIIa is reacted with NaBH₄.

10. The method of claim 5, wherein the compound represented by structural formula XIIIa is reacted with R₈MgBr.

11. The method of claim 1 for preparing the compound represented by structural formula XIIIa:

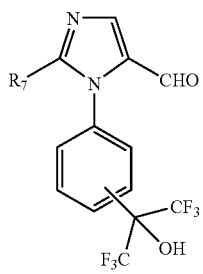

XIIIa wherein
the compound represented by structural formula XI is formed by treating the aniline derivative represented by structural formula III with R₇CN in the presence of aluminum chloride; and

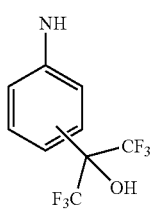

III

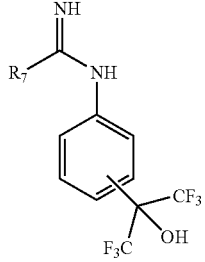

XI the compound represented by structural formula XIIIa is formed by treating the compound represented by structural formula XI with an α-bromoaldehyde,
wherein R₇ is hydrogen, alkyl, aryl, heterocyclyl, or acyl.

12. The method of claim 5, wherein
the compound represented by structural formula XI is formed by treating the aniline derivative represented by structural formula III with R₇CN in the presence of aluminum chloride;

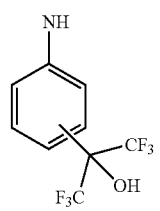

III

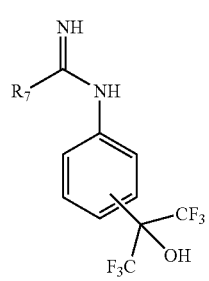

XI the compound represented by structural formulae XIIIa is formed by treating the compound represented by structural formula XI with an α-bromoaldehyde;

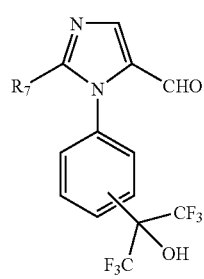

XIIIa the compound represented by the following structural formula:

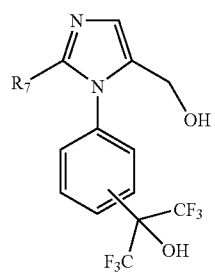

is formed by reacting the compound represented by structural formula XIIIa with NaBH₄,
wherein
R₇ is hydrogen, alkyl, aryl, heterocyclyl, or acyl; and
R₈ is hydrogen.

* * * * *